(12) United States Patent
Goetz et al.

(10) Patent No.: US 11,126,270 B2
(45) Date of Patent: *Sep. 21, 2021

(54) SYSTEMS AND METHODS FOR MITIGATING GESTURE INPUT ERROR

(71) Applicant: Medtronic, Inc., Minneapolis, MN (US)

(72) Inventors: Steven M. Goetz, North Oaks, MN (US); Pedram Afshar, San Francisco, CA (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/806,889

(22) Filed: Mar. 2, 2020

(65) Prior Publication Data

US 2020/0201447 A1 Jun. 25, 2020

Related U.S. Application Data

(63) Continuation of application No. 14/607,885, filed on Jan. 28, 2015, now Pat. No. 10,613,637.

(51) Int. Cl.
| | | |
|---|---|---|
| *G06F 3/01* | (2006.01) | |
| *G06F 3/03* | (2006.01) | |
| *G16H 40/63* | (2018.01) | |

(52) U.S. Cl.
CPC ............ *G06F 3/017* (2013.01); *G06F 3/0304* (2013.01); *G16H 40/63* (2018.01)

(58) Field of Classification Search
CPC ........ G06F 3/017; G06F 3/0304; G16H 40/63
See application file for complete search history.

(56) References Cited

U.S. PATENT DOCUMENTS

| 5,570,113 A | 10/1996 | Zetts |
| 5,805,725 A | 9/1998 | Sakata et al. |

(Continued)

FOREIGN PATENT DOCUMENTS

| CN | 102999288 A | 3/2013 |
| WO | 2012129669 A1 | 10/2012 |

(Continued)

OTHER PUBLICATIONS

"Future surgeons may use robotic nurse, 'gesture recognition'" Purdue University, University News Service, Feb. 3, 2011, retrieved from https://www.purdue.edu/newsroom/research/20111110203WachsGestures.html.

(Continued)

*Primary Examiner* — Phenuel S Salomon
(74) *Attorney, Agent, or Firm* — Shumaker & Sieffert, P.A.

(57) ABSTRACT

Devices, systems, and techniques for mitigating error from gesture input are disclosed. A system may receive an indication of a first gesture input, determine that the first gesture input is an indicator gesture input, and, responsive to the determination that the first gesture input is the indicator gesture input, enter a gesture control mode during which the system is configured to control one or more actions related to a medical procedure. Only during the gesture control mode, the system may receive an indication of a second gesture input associated with the medical procedure and, responsive to receiving the indication of the second gesture input, control, based on the second gesture input, at least a portion of the medical procedure. Additionally, or alternatively, the system may employ other error mitigation techniques for gesture input related to medical procedures.

21 Claims, 17 Drawing Sheets

(56) References Cited

U.S. PATENT DOCUMENTS

| | | |
|---|---|---|
| 6,353,764 B1 | 3/2002 | Imagawa et al. |
| 6,711,442 B1 | 3/2004 | Swerdlow |
| 7,274,290 B2 | 9/2007 | Morita et al. |
| 7,502,742 B2 | 3/2009 | Knott et al. |
| 7,930,633 B2 | 4/2011 | Suzuki et al. |
| 8,078,560 B2 | 12/2011 | Takata et al. |
| 8,411,034 B2 | 4/2013 | Boillot et al. |
| 8,417,342 B1* | 4/2013 | Abell .................. A61B 5/4836 607/40 |
| 8,421,761 B2 | 4/2013 | Natanzon et al. |
| 8,428,368 B2 | 4/2013 | Ivanich et al. |
| 8,863,040 B2 | 10/2014 | Queru |
| 9,123,341 B2 | 9/2015 | Weng |
| 9,393,699 B1 | 7/2016 | Jules et al. |
| 9,483,122 B2 | 11/2016 | Grass |
| 10,133,397 B1* | 11/2018 | Smith .................. G06F 3/0416 |
| 10,613,637 B2 | 4/2020 | Goetz et al. |
| 2005/0025706 A1 | 2/2005 | Kagermeier |
| 2005/0102167 A1 | 5/2005 | Kapoor |
| 2007/0016008 A1* | 1/2007 | Schoenefeld .......... A61B 90/36 600/424 |
| 2007/0118400 A1 | 5/2007 | Morita et al. |
| 2008/0104547 A1 | 5/2008 | Morita et al. |
| 2008/0114226 A1 | 5/2008 | Music |
| 2008/0253519 A1 | 10/2008 | Bonfiglio et al. |
| 2009/0021475 A1* | 1/2009 | Steinle .................... G06F 19/00 345/156 |
| 2009/0213123 A1* | 8/2009 | Crow ................ G06K 9/00342 345/473 |
| 2009/0275805 A1 | 11/2009 | Lane et al. |
| 2010/0169842 A1 | 7/2010 | Migos |
| 2010/0174155 A1 | 7/2010 | Heruth et al. |
| 2010/0281435 A1 | 11/2010 | Bangalore et al. |
| 2010/0306712 A1* | 12/2010 | Snook ................ G06K 9/00342 715/863 |
| 2011/0040404 A1 | 2/2011 | Diolaiti et al. |
| 2011/0093821 A1 | 4/2011 | Wigdor et al. |
| 2011/0185309 A1* | 7/2011 | Challinor ................ A63F 13/42 715/784 |
| 2011/0307032 A1 | 12/2011 | Goetz et al. |
| 2012/0016641 A1 | 1/2012 | Raffa |
| 2012/0056801 A1 | 3/2012 | Bevilacqua et al. |
| 2012/0092355 A1 | 4/2012 | Yamamoto et al. |
| 2012/0154294 A1* | 6/2012 | Hinckley ............. G06F 1/1677 345/173 |
| 2012/0169624 A1 | 7/2012 | Gam |
| 2012/0229383 A1 | 9/2012 | Hamilton et al. |
| 2012/0283894 A1 | 11/2012 | Naboulsi et al. |
| 2012/0306770 A1 | 12/2012 | Moore et al. |
| 2012/0323364 A1 | 12/2012 | Birkenbach et al. |
| 2013/0106899 A1 | 5/2013 | Bhatt |
| 2013/0144629 A1 | 6/2013 | Johnston et al. |
| 2013/0154913 A1 | 6/2013 | Gene et al. |
| 2013/0179162 A1 | 7/2013 | Merschon et al. |
| 2013/0204428 A1 | 8/2013 | Steinle et al. |
| 2013/0225999 A1 | 8/2013 | Banjanin et al. |
| 2013/0263251 A1 | 10/2013 | Fleizach et al. |
| 2013/0271397 A1 | 10/2013 | MacDougall |
| 2014/0049465 A1* | 2/2014 | Tremaine ........... G06K 9/00201 345/156 |
| 2014/0168062 A1* | 6/2014 | Katz ..................... G06F 3/0484 345/156 |
| 2014/0181716 A1 | 6/2014 | Merritt |
| 2014/0181761 A1* | 6/2014 | Fischer .................. G06F 30/39 716/52 |
| 2014/0195986 A1 | 7/2014 | Li |
| 2014/0298672 A1* | 10/2014 | Straker ................. H04W 12/06 34/175 |
| 2014/0331175 A1 | 11/2014 | Havilio |
| 2014/0359450 A1 | 12/2014 | Lehtiniemi et al. |
| 2015/0074615 A1 | 3/2015 | Han et al. |
| 2015/0261318 A1 | 9/2015 | Scavezze et al. |
| 2015/0302179 A1 | 10/2015 | Rheault |
| 2015/0355716 A1 | 12/2015 | Balasubramanian |
| 2015/0370318 A1 | 12/2015 | Yamaguchi et al. |
| 2016/0071341 A1* | 3/2016 | Menzel ................. A61B 90/90 340/5.61 |
| 2016/0216768 A1 | 7/2016 | Goetz et al. |
| 2016/0378939 A1 | 12/2016 | Baumberger |
| 2017/0205963 A1 | 7/2017 | Havilio |

FOREIGN PATENT DOCUMENTS

| | | |
|---|---|---|
| WO | 2013035001 A2 | 3/2013 |
| WO | 2013149586 A1 | 10/2013 |
| WO | 2013168056 A1 | 11/2013 |

OTHER PUBLICATIONS

Prosecution History from U.S. Appl. No. 14/607,866, dated Oct. 30, 2017 through Apr. 16, 2020, 260 pp.

Prosecution History from U.S. Appl. No. 14/607,885, dated Jun. 30, 2017 through Mar. 6, 2020, 308 pp.

Reply Brief Responsive to Examiner's Answer dated Apr. 16, 2020, from U.S. Appl. No. 14/607,866, filed Jun. 16, 2020, 9 pp.

Decision on Appeal from U.S. Appl. No. 14/607,866, dated May 6, 2021, 8 pp.

Response to the Decision on Appeal dated May 6, 2021, from U.S. Appl. No. 14/607,866, filed Jul. 6, 2021, 15 pp.

* cited by examiner

SYSTEMS AND METHODS FOR MITIGATING GESTURE INPUT ERROR

This application is a continuation of U.S. patent application Ser. No. 14/607,885, filed Jan. 28, 2015, the entire contents of which are incorporated herein by reference.

TECHNICAL FIELD

The disclosure relates to medical systems and, more particularly, medical system user interfaces.

BACKGROUND

A computing device (e.g., a workstation, surgical suite, programming device, tablet computer, and notebook computer) typically utilizes one or more input devices that convert user provided input into electrical signals representing the user input and interpretable by the computing device. Example input devices may include keyboards, mice, joysticks, touch pads, dedicated hardware buttons, touch screens, microphones, and cameras. Through use of one or more of these input devices, a user may interface with one or more applications executing on the computing device. For example, the user may start or terminate an application, input data into the application, request the application to retrieve data stored in a data storage device, or command the application to control a computer-controlled machine to perform one or more tasks.

SUMMARY

In general, devices, systems, and techniques for mitigating error from gesture input in a medical system are described. A medical system may control one or more actions related to a medical procedure based on gesture inputs received from a user, e.g., a clinician. One or more sensors, e.g., camera-based sensors or presence-sensitive sensors, may be configured to detect hand motions or hand configurations presented by the user as gesture input requesting that the system control an action related to the medical procedure. The system may incorporate one or more mechanisms for mitigating error that may occur when detecting such gesture input. For example, the system may require an indicator gesture input or determination of a particular step in a medical procedure that triggers entry into a gesture control mode during which the system can receive gesture input to control one or more actions. In another example, the system may terminate the gesture control mode responsive to a time-out period or completion of the step of the medical procedure. In some examples, the system may limit the rate of change or adjustment range for adjustments to a medical procedure parameter made using a gesture input. These and other error mitigation techniques described herein may be used alone or in combination when receiving gesture input.

In one example, the disclosure is directed to a method including receiving, by a processor, an indication of a first gesture input, determining, by the processor, that the first gesture input is an indicator gesture input, responsive to the determination that the first gesture input is the indicator gesture input, entering, by the processor, a gesture control mode during which the processor is configured to control one or more actions related to a medical procedure, receiving, by the processor and during the gesture control mode, an indication of a second gesture input associated with the medical procedure, and responsive to receiving the indication of the second gesture input, controlling, by the processor and based on the second gesture input, at least a portion of the medical procedure.

In another example, the disclosure is directed to a system that includes one or more processors configured to receive an indication of a first gesture input, determine that the first gesture input is an indicator gesture input, responsive to the determination that the first gesture input is the indicator gesture input, enter a gesture control mode during which the processor is configured to control one or more actions related to a medical procedure, receive, during the gesture control mode, an indication of a second gesture input associated with the medical procedure, and responsive to receiving the indication of the second gesture input, control, based on the second gesture input, at least a portion of the medical procedure.

In another example, the disclosure is directed to a computer-readable storage medium including instructions that, when executed, cause one or more processors to receive an indication of a first gesture input, determine that the first gesture input is an indicator gesture input, responsive to the determination that the first gesture input is the indicator gesture input, enter a gesture control mode during which the processor is configured to control one or more actions related to a medical procedure, receive, during the gesture control mode, an indication of a second gesture input associated with the medical procedure, and, responsive to receiving the indication of the second gesture input, control, based on the second gesture input, at least a portion of the medical procedure.

In another example, the disclosure is directed to a method that includes receiving, by a processor, an indication to enter a gesture control mode during which the processor is configured to control one or more actions related to a medical procedure, responsive to receiving the indication, entering, by the processor, the gesture control mode, monitoring, by the processor, field input data received during the gesture control mode for one or more control gesture inputs, the one or more control gesture inputs requesting the processor control the one or more actions related to the medical procedure, determining, by the processor and during the gesture control mode, to exit the gesture control mode, and responsive to determining to exit the gesture control mode, exiting, by the processor, the gesture control mode, wherein exiting the gesture control mode disables gesture input control of the one or more actions related to the medical procedure.

In another example, the disclosure is directed to a system that includes one or more processors configured to receive an indication to enter a gesture control mode during which the processor is configured to control one or more actions related to a medical procedure, responsive to receiving the indication, enter the gesture control mode, monitor field input data received during the gesture control mode for one or more control gesture inputs, the one or more control gesture inputs requesting the processor control the one or more actions related to the medical procedure, determine, during the gesture control mode, to exit the gesture control mode, and, responsive to determining to exit the gesture control mode, exit the gesture control mode, wherein exiting the gesture control mode disables gesture input control of the one or more actions related to the medical procedure.

In another example, the disclosure is directed to a computer-readable storage medium including instructions that, when executed, cause one or more processors to receive an indication to enter a gesture control mode during which the processor is configured to control one or more actions related to a medical procedure, responsive to receiving the indication, enter the gesture control mode, monitor field input data received during the gesture control mode for one or more control gesture inputs, the one or more control gesture inputs requesting the processor control the one or more actions related to the medical procedure, determine, during the gesture control mode, to exit the gesture control mode, and responsive to determining to exit the gesture control mode, exit the gesture control mode, wherein exiting the gesture control mode disables gesture input control of the one or more actions related to the medical procedure.

The details of one or more example are set forth in the accompanying drawings and the description below. Other features, objects, and advantages will be apparent from the description and drawings, and from the claims.

DETAILED DESCRIPTION

Figure 1:
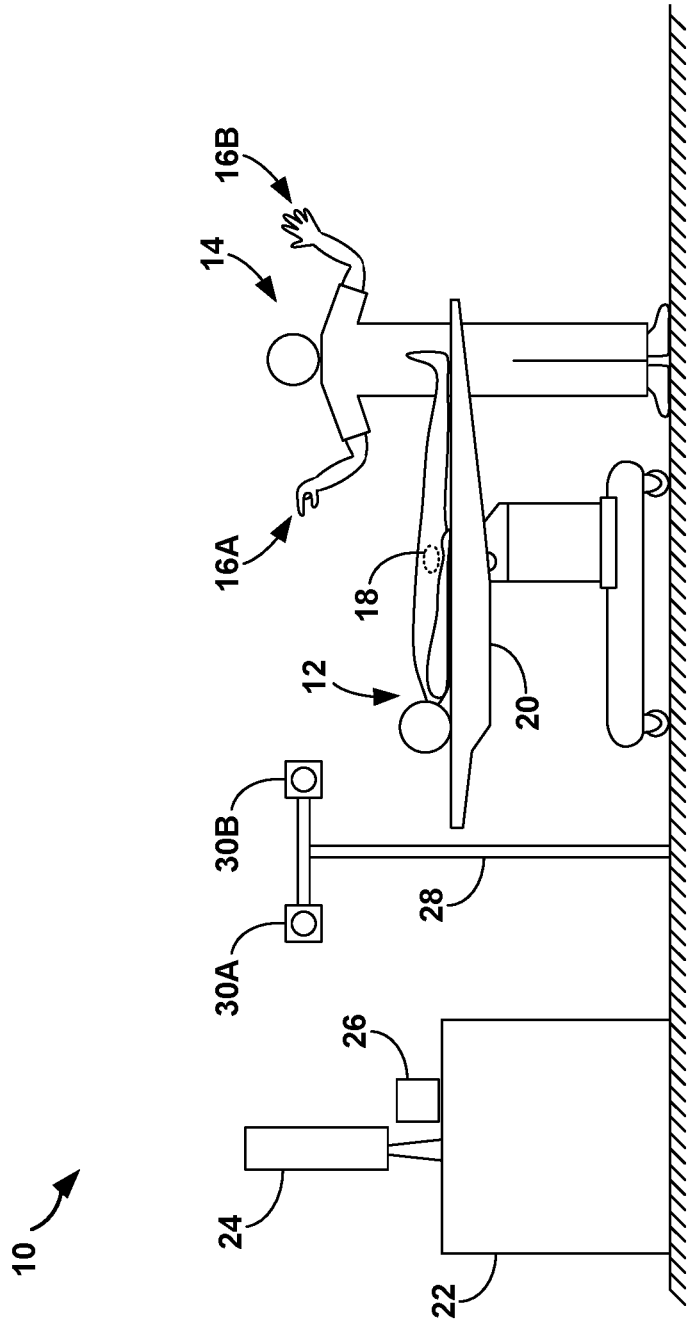
FIG. 1 is a conceptual diagram illustrating an example system that includes a gesture control system for controlling one or more actions of a medical procedure based on received gesture input.

This disclosure is generally directed to devices, systems, and techniques for mitigating error that may occur due to gesture input control of medical procedures. Gesture interfaces, those user interfaces which are configured to receive gesture input from a user (e.g., stationary hand positions, hand movements, or some combination thereof), provide flexible mechanisms for computer-human interaction. A system utilizing gesture input may provide unique input mechanisms appropriate for a variety of actions, reduce input complexity, and/or eliminate the need for the user to physically touch an input device.

However, the detection of hand movements or hand positions in gesture interfaces includes an inherent increase in probability of detecting inadvertent or unwanted gestures that result in the system performing an unintended action. In the context of consumer electronic devices, these unintended actions may be of low consequence because correcting the unintended action may only require an additional navigation step through the user interface or providing another input that will "undo" or reverse the previous unintended input. In contrast, inadvertent gesture input provided to a system that controls a medical procedure may result in an unintended action of high consequence to a patient receiving the medical procedure.

As discussed herein, systems may be configured to receive and manage gesture input to reduce or eliminate gesture input-related errors for medical procedures. A system may control one or more actions related to a medical procedure based on one or more gesture inputs received from a user, e.g., a clinician or a patient. One or more sensors, e.g., camera-based sensors, capacitive sensors, resistor sensors or presence-sensitive sensors, may be configured to detect hand motions or hand configurations presented by the user as gesture input requesting that the system control an action related to the medical procedure. The system may incorporate one or more mechanisms for mitigating error that may occur when detecting such gesture input. For example, a gesture control system (e.g., one or more of a standalone computing device, a networked server, and/or external programmer) may be configured to only receive gesture input that controls an action of a medical procedure during a gesture control mode. The system may initiate gesture control mode in response to receiving an indication gesture input or determining that a predetermined step during the medical procedure as started. The system may exit, or stop, the gesture control mode in response to receiving a termination gesture input or determining that a predetermined step during the medical procedure has ended.

In addition, or alternative, to implementing a gesture control mode, a system may be configured to ensure that a gesture input is received from a known user. For example, the system may be configured to detect any unexpected object within an envelope within which the gesture input is detected. The unexpected object may be the hand of a second user, an object attached to the user's hand or finger, or any other abnormality that reduces the accuracy of gesture input detection from the user. In some examples, changes in lighting or a change in the angle between a gesture sensor and the user may manifest as the detection of an unexpected object. In response to detection of an unexpected object, the system may suspend a gesture control mode or otherwise lockout gesture input control of any actions related to the medical procedure.

A system may also mitigate error with gesture input by limiting the magnitude of any adjustment that can be changed by gesture input. The system may apply a factor to gesture input that limits a rate of change or adjustment range for any action controlled by gesture input. For example, the factor may establish a small rate of change for any adjustments made using gesture input such that a gesture input cannot unintentionally cause large or drastic actions during the medical procedure. The system may also set an adjustment range specific to gesture input such that the system only changes a parameter value within a limited or small range in response to gesture input. In this manner, the system may require increased duration and/or magnitude of a gesture input to adjust a parameter to the same degree as a smaller adjustment via a physical button or knob.

A gesture control system may employ one or any combination of techniques to minimize or eliminate error that may occur when controlling actions based on gesture input. Employment of such error mitigation techniques may improve gesture interface technologies and systems related to control of medical devices during medical procedures. These error mitigation techniques may also improve the functioning of control systems by reducing computations required to process gesture input when gesture input cannot be used for control or reducing the computational resources needed to correct unintended user input that may occur without such error mitigation techniques. A system employing error mitigation techniques described herein may also decrease user fatigue by reducing or eliminating unintended gesture input that requires correction by the user.

FIG. 1 is a conceptual diagram illustrating example system 10 that includes a gesture control device 22 for controlling one or more actions of a medical procedure based on received gesture input from user 14. As shown in FIG. 1, system 10 may include gesture control device 22, output devices 24 and 26, camera-based sensors 30A and 30B (collectively "sensors 30"), operating table 20, and implantable medical device (IMD 18). Patient 12 is shown as lying down on operating table 20 and with IMD 18 implanted within patient 12. IMD 18 may or may not have been implanted during the medical procedure example in system 10. IMD 18 may be configured to deliver a therapy to patient 12. User 14 (e.g., a clinician or other healthcare professional) may provide gestures detectable by one or more of sensors 30 and interpretable by gesture control device 22 as gesture input that controls one or more actions related to a medical procedure being performed on patient 12. In some examples, system 10 may also include an external programmer (not shown) configured to communicate with and program operations of IMD 18 and/or communicate with gesture control device 22.

A medical procedure may include any actions related to a medical patient, such as diagnosis and/or treatment of patient 12. Example medical procedures may also include manual examination by a physician, non-invasive data collection and/or imaging, removal of a fluid or tissue sample, surgical intervention, implantation of a medical device, adjustment or removal of a medical device from tissue, or adjustment of one or more therapy parameters that at least partially define delivery of therapy from a medical device or monitoring of a patient. In this manner, the medical procedure may include actions provided by a medical professional for the purpose of examining, diagnosing, or treating the patient. Medical procedures may be any action performed by a medical professional (e.g., a physician, clinician, or nurse) in relation to a patient or in association with one or more computing devices or medical devices associated with the diagnosis or treatment of the patient.

System 10 may be configured to capture, or detect, gestures performed by user 14 during a medical procedure. In one example, user 14 may use one or both of hands 16A and 16B to make gestures detectable by one or more sensors 30. Gestures may include specific locations within a detectable envelope, stationary configurations and/or movements of one or more fingers or hands. For example, gestures may include a predetermined number of extended fingers, a shape of one or more fingers or hands, a spatial relationship of one or more fingers to another one or more fingers, a movement of one or more fingers or hands to another one or more fingers or hands, or any combination thereof. Although gestures will be generally described with relation to fingers and/or hands, a gesture may involve one or more other portions of the anatomy of user 14. In some examples, gestures may be performed by multiple users.

Sensors 30A and 30B may be configured to detect gestures performed by user 14 and generate a signal representative of the detected gestures. Sensors 30A and 30B may be camera-based sensors that obtain light reflected off of user 14. Sensors 30 are shown as mounted onto stand 28 to position sensors 30 in front of user 14, but sensors 30 may be attached to any structure or otherwise positioned to detect the gestures of user 14. For examples, sensor 30A and/or sensor 30B may include one or more sensors (e.g., charge-coupled device (CCD) or complementary metal-oxide-semiconductor (CMOS)) configured to convert visible light to electrical signals representing the visible light. In other examples, sensors 30 may include other sensors that are configured to capture infra-red electromagnetic radiation and/or any other medium representative of the position or movement of user 14. In some examples, sensors 30 may include electrical field sensors, heat sensors, or any sensors configured to detect the position and/or movement of user 14 within a location envelope detectable by the sensors. Sensors 30 may, in some examples, include capacitive or resistive sensors associated with a touchscreen device.

As shown in the example of FIG. 1, system 10 may include two sensors 30 to generate stereo images (or multiple vantage points) of user 14 that includes depth of field instead of single plane information typically generated from a single sensor. In this manner, sensors 30 may be configured to detect hands 16A and 16B in three dimensions and locate where hands 16 are located within the space of the room in which sensors 30 are located. In some examples, gesture control device 22 may use this spatial information of hands 16 within the room to determine which gesture input has been provided. For example, gesture control device 22 may determine a particular gesture input is associated with control of a first device when the gesture input is detected in a particular corner of the room as opposed to the particular gesture input being associated with control of a second device when the gesture input is detected adjacent to patient 12. In this manner, gesture control device 22 may use identified items around the room and in relation to hands 16 to determine the functionality to which the gesture input should be applied (e.g., hands 16 within a spatial envelope of a device control that device or hands 16 within a special envelope of patient 12 control parameters of IMD 18). Using the spatial location of gestures within the detection area of sensors 30 may provide a larger vocabulary of gesture inputs. In other words, the same gesture could be combined with the spatial data of where the gesture was detected in order to generate multiple different gesture inputs (e.g., the gesture input is based on the gesture and the spatial location of the gesture within the room).

In some examples, three or more sensors may be used to detect gestures provided by user 14. Multiple sensors (e.g., sensors 30A and 30B) may be of the same type or sensing modality (e.g., all optical sensors or all ultrasonic sensors) or of different types or sensing modalities (e.g., an optical sensor, an infrared sensor, and an ultrasonic sensor) to minimize error conditions that may not affect all of the different types of sensors. The sensing modality may be specific to the physical medium through which the sensor detects the gestures (e.g., frequencies of light, heat, vibrations, sound or pressure waves, electrical fields, etc.). In other words, system 10 may provide more robust detection of gestures by detecting the gestures using multiple types of detection modalities. If one of the modalities is compromised, such as lighting changes for an optical sensor or electronic interference for another type of sensor, the one or more additional modalities may remain operational and sufficient to detect the gestures provided by user 14.

In other examples, a single sensor may be configured to detect gestures instead of multiple sensors. Sensors configured to detect gestures may be placed at a variety of locations within an operating room, examination room, or any other environment within which gestures are to be detected. For example, system 10 may include one or more sensors above user 14 and patient 12 (e.g., sensors attached to a ceiling mount or overhead mount), below user 14 and patient 12 (e.g., sensors within or on the floor and/or operating table 20), attached to gesture control device 22, or even attached to patient 12 and/or user 14. In some examples, user 14 may wear one or more devices detectable by sensors 30 to facilitate or improve the detection of user gestures.

Sensors 30 may generate one or more signals representative of the detected gestures, and the signals may be referred to as field input data. Sensors 30 may transmit the field input data to one or more processors of gesture control device 22 via a wired and/or wireless connection. Gesture control device 22 may receive the field input data, determine when one or more detected gestures result in a respective gesture input, and determine what actions to take in response to the gesture input. Gesture control device 22 may compare the gesture input to predetermined gesture inputs stored in memory, or interface with a networked computing device that performs the comparison, to determine the request of each gesture input. In addition, gesture control device 22 may employ one or more of the error mitigation techniques described herein in order limit gesture inputs to those gesture inputs actually intended to be detected from user 14.

Gesture control device 22 may be configured to output information related to gesture inputs to user 14. Gesture control device 22 may be in communication with display 24 (e.g., an output device) and speaker 26 (e.g., another output device). Gesture control device 22 may control display 24 and/or speaker 26 to deliver information to user 14 regarding the gesture input and/or actions controlled by the gesture input for the medical procedure. Display 24 may display, based on output and/or instructions generated by gesture control device 22, visual information such as the most recent gestures detected, the resulting gesture input, and/or what actions will be controlled based on the gesture input.

In addition, display 24 may be configured to present information regarding the interaction mode of gesture control device 22. For example, display 24 may display an indication of the type of gesture interaction mode currently used by gesture control device 22. The indication may indicate whether gesture control is active (or "on" to indicate that the system is currently detecting gestures or using gesture input) or inactive (or "off" to indicate that the system is not currently detecting gestures or using gesture input). In some examples, the indication may alternatively, or additionally, indicate the type of gesture interaction mode used to detect gestures from user 14. For example, the type of interaction mode indicated may be representative of the modality used to detect gestures (e.g., optical, infrared, or ultrasonic) and/or the sensors used to detect gestures. The indication of the gesture interaction mode may include one or more pictures or symbols (e.g., a graphical icon), words, characters, numerical representations, colors, shading variations for respective modes, or any other visual representation of the type of gesture interaction mode currently used by gesture control device 22.

Speaker 26 may deliver audio information regarding the gesture input in addition to, or alternative to, display 24. User 14 may utilize information delivered by gesture control device 22 via display 24 and/or speaker 26 to ensure that gesture input is correct. Gesture control device 22 may also output, via display 24 and/or speaker 26, an indication of when the gesture control mode has been entered and/or what step is currently active for the medical procedure.

Gesture control device 22 may interface with one or more medical devices configured to perform an action related to a medical procedure for patient 12. In this manner, gesture control device 22 may control, based on received gesture input, the one or more medical devices. Gesture control device 22 may be in communication with the medical devices via wired and/or wireless communication protocols. For example, the controlled medical device may be a surgical device configured to operate on patient 12 (e.g., a device configured to cut, pierce, ablate, remove, attach, or mend patient tissue). In one example, gesture control device 22 may be configured to control the surgical device to deliver ablation energy to patient 12 in response to receiving the corresponding control gesture input. In other examples, the controlled medical device may be a surgical device configured to implant, or assist with the implantation of, one or more additional medical devices. In one example, gesture control device 22 may be configured to control the position of a catheter insertion device based on received gesture input. In this manner, gesture control device 22 may be configured to control of a surgical device to operate with respect to patient 14 receiving the medical procedure. In some examples, the controlled medical device may be an external or implantable medical device configured to remain with patient 12 outside of the clinic and provide therapy to and/or monitor physiological status of, patient 12. In this manner, gesture control device 22 may be configured to adjust, based on the received gesture input, a parameter value of one or more parameters that at least partially defines a medical therapy.

A medical procedure that may be at least partially controlled by gesture input includes surgical procedures, such as the removal or repair of patient tissue or implantation of one or more medical devices. In other examples, a medical procedure that may be at least partially controlled by gesture input may include the adjustment of one or more parameters that at least partially define a therapy delivered by a medical device. For example, the therapy may be an electrical stimulation therapy delivered by an implantable medical device. Alternatively, the therapy may be a drug delivery therapy delivered by an implantable medical device.

As described herein, system 10 may be configured to employ one or more error mitigation techniques for gesture input interfaces. For example, gesture control device 22 may be configured to receive an indication of a first gesture input and determine that the first gesture input is an indicator gesture input. Responsive to the determination that the first gesture input is the indicator gesture input, gesture control device 22 may be configured to enter a gesture control mode during which the processor is configured to control one or more actions related to a medical procedure and receive, during the gesture control mode, an indication of a second gesture input associated with the medical procedure. Gesture control device 22 may then, responsive to receiving the indication of the second gesture input, control, based on the second gesture input, at least a portion of the medical procedure.

Gesture control device 22 may be configured to also output, for display via a user interface, an indication that the gesture control mode is entered. For example, gesture control device 22 may control display 24 and/or speaker 26 to present a visual and/or audible indication to user 14 that the gesture control mode has been entered and gesture input can be used for control of the medical procedure. One or more of camera-based sensors 30 may be configured to sense the first and second inputs from user 14 and transmit the gesture input to gesture control device 22 as field input data. In some examples, gesture control device 22 may determine from the field input data whether or not a gesture input has occurred. Alternatively, gesture control device 22 may receive an indication of what gesture input was detected and then determine what action to take for the corresponding gesture input that was received.

The first and second gesture input received by gesture control device 22 may be indicative of certain types of gesture input. For example, the second gesture input that is received during the gesture control mode may be one of a plurality of pre-defined control gestures that are detectable. In other words, the control gestures may be stored in a library of control gestures such that gesture control device 22 can determine when a control gesture has been provided by user 14. The first gesture input may be described as an indicator gesture input requesting entry into the gesture control mode so that control gesture input can be utilized by gesture control device 22. In some examples, the indicator gesture input may be different from any of the possible control gesture input such that the gesture input controlling the gesture control mode status (e.g., whether the gesture control mode has been entered or not) remains separate from any gesture input used to control the one or more actions related to the medical procedure. This separation may, in some examples, reduce the possibility that the gesture control mode is inadvertently entered. Gesture control device 22, or another computing device that stores and/or manages the library of control gestures, may be configured to create, update, or otherwise manage the control gestures stored in the library in response to user input requesting a change to the library. In this manner, the library may be configurable, selectable, and/or created according to input provided by one or more users. In this manner, the library may be configured to be specific for one or more specific purposes and/or one or more specific users. The library may also include indicator gestures or any other types of gestures in addition to, or alternative to, control gestures.

In some examples, the indictor gesture input may be a low-error gesture input that is easily detected by gesture control device 22. Example low-error gesture inputs may include those gestures with multiple identifiable portions of the anatomy of user 14 (e.g., five outstretched fingers of one hand or one hand positioned in relation to another portion of the user anatomy such as the nose or ear). In contrast, control gesture inputs may not be low-error gesture input because the control gesture input may include motion or some other complex hand configuration needed to indicate a desired change in the medical procedure. Gesture inputs that are not specifically classified as "low-error" gestures herein are not necessarily prone to high error or otherwise compromise the accuracy of the gesture input or the corresponding action requested by the gesture input. For example, some gestures used for control gesture input (e.g., moving two fingers together to indicate reducing a parameter value) may involve determining changes to a hand in space, but such a gesture may still provide sufficient specificity for a control gesture input. However, low-error gesture inputs may be particularly resistant to error in the user making the gesture and/or gesture control device 22 detecting the gesture. As described herein, confirmation gesture input and/or termination gesture input may also be selected with low-error gestures in some examples. Control gesture input may be low-error gestures in some examples, but the control scheme may only allow pre-selected changes or small incremental changes in the adjusted control of the corresponding action of the medical procedure.

In some examples, gesture control device 22, or another computing device associated with system 10, may be configured to classify gestures as low-error gestures, high-error gestures, or provide a scale indicative of the relative ease at which gesture control device 22 can accurately identify the gesture from a user. The computing device may thus analyze a particular gesture for qualitative and/or quantitative measure of the error rates for particular gestures. This measure may be a scale indicating the relative error rates for each of a plurality of gestures. The relative error rate for a given gesture may be retrieved from a stored databased of predetermined error rates for types of gestures and/or calculated based on the gesture selected for use. For example, the gesture control device 22 may recognize attributes of the gesture (e.g., stationary, motion, range of motion, speed of motion, number of fingers, number of hands, duration of gesture, steps in each gesture, size of detectable elements in the gesture, etc.) and assign an expected error value to each of these attributes. For example, gesture control device 22 may apply a higher expected error value to motion attributes than stationary attributes. Gesture control device 22 may then calculate an error rate for the gesture based on the error values of each attribute (e.g., a sum of the error values or weighted average of the error values).

Based on the error rate for a gesture, gesture control device 22 may control a display to present an indication of the error rate for the gesture. The indication may be the actual error rate value or a classification of the error rate within two or more groups (e.g., a low-error gesture and a high-error gesture) or along a scale of three or more levels of error. The user can use the classification or error rate to determine to which functionality the gesture can be used for control or indicator gestures. In some examples, gesture control device 22 may control the display to present an error or confirmation message if the error rate or classification of the gesture is not suitable for the selected functionality requested to be controlled by the gesture. Gesture control device 22 may request confirmation input (or even reject the assignment of a gesture to a user selected function) for high-error gestures selected to control high risk activities associated with patient 12. For example, gesture control device 22 may prompt user 14 to confirm that a high-error gesture of a complex hand motion gesture should be assigned to control the initiation and termination of ablation energy. In other words, such high risk activity may be more suitably controlled by a low-error gesture such as a stationary hand with five outstretched fingers. If gesture control device 22 rejects the assignment of a gesture to a particular function or activity, gesture control device 22 may present an error message to user 14 indicating the rejection of the gesture assignment and, in some examples, an explanation for why the gesture was not assigned to the function.

Gesture control device 22 may exit the gesture control mode based on one or more exit triggers. The exit triggers may be provided to prevent the gesture control mode from remaining active for periods of time during which gesture input may be inadvertent (e.g., during portions of the medical procedure in which gesture inputs should not be used for control or after the period of time a user requires gesture input for control of the medical procedure). In other words, limiting the period of time during which gesture input can control one or more actions of a medical procedure may limit errors related to gesture input such as inadvertent gesture inputs.

In one example, gesture control device 22 may be configured to track a duration of time from when the gesture control mode was entered, compare the duration of time to a predetermined gesture control timeout, and determine that the duration of time exceeds the predetermined gesture control timeout. Responsive to determining that the duration of time exceeds the predetermined gesture control timeout, gesture control device 22 may exit the gesture control mode. In this manner, the predetermined gesture control timeout may define the predetermined period of time during which a gesture control mode may remain active. For example, the predetermined gesture control timeout may be between approximately 10 seconds and 2 hours. In another example, the predetermined gesture control timeout may be between 1 minute and 5 minutes. The gesture control timeout may be selected by gesture control device 22 based on a specific medical procedure and/or a particular step within a medical procedure such that the duration of the gesture control timeout is matched to the length of time the user needs the gesture control mode to be active to perform a particular action of the medical procedure and/or the entire medical procedure. In some examples, gesture control device 22 may be configured to receive a user input (e.g., a mechanical or gesture input) requesting an extension to the predetermined gesture control timeout. Gesture control device 22 may grant the request to the extension in all cases or only in response to determining that the medical procedure, or step of the medical procedure, allows for extensions to the gesture control timeout.

In another example, gesture control device 22 may exit the gesture control mode based on the progress of the medical procedure. Gesture control device 22 may be configured to monitor progress of the medical procedure, where the medical procedure includes a plurality of steps. At least one of the plurality of steps may be configured to accept gesture input for control of an action corresponding to the step. In some examples, initiation gesture input and/or control gesture input may be received during the duration of the step of the medical procedure. Gesture control device 22 may determine that the one step of the medical procedure has been completed (e.g., based on an input received that defines the completion of the step or identifying that a subsequent step for the medical procedure has started). In some examples, gesture control device 22 may determine that a step of the medical procedure has been completed in response to detecting or identifying use of other devices or instruments (e.g., a surgical instrument or other computing device). In one example, gesture control device 22 may determine that the surgical planning step has been completed in response to detecting that a surgical navigation system and/or user interface has been activated. Responsive to determining that the one step has been completed, gesture control device 22 may exit the gesture control mode. In some examples, the gesture control mode may span two or more steps of the medical procedure such that gesture control device 22 enters the gesture control mode during one step of the medical procedure and exits the gesture control mode after completion of a different and subsequent step of the medical procedure. In this manner, the gesture control mode may only be active, or entered, during steps of the medical procedure appropriate for gesture input control of one or more actions.

Alternative, or in addition, to other exit triggers, gesture control device 22 may be configured to exit or suspend the gesture control mode in response to detecting unexpected objects (e.g., objects, anomalies, motions, etc.) in an envelope within which gestures from user 14 can be detected by sensors 30, for example. In one example, gesture control device 22 may receive field input data from sensors 30 during the gesture control mode (e.g., when the gesture control mode is entered or active). Gesture control device 22 may detect, from the field input data, an unexpected object in the envelope within which a previous gesture input was sensed or a gesture input is otherwise detectable. The unexpected object may be a third hand or other anatomical structure (which may indicate a second user has entered the envelope), a device (e.g., a medical device such as a surgical instrument) in or attached to one of hands 16 of user 14, an object that obstructs the view of at least a portion of the envelope from one or more or sensors 30, or any other anomaly that may increase the probability of an inadvertent gesture input and/or limit the ability of gesture control device 22 to accurately detect gesture input. Example anomalies detected by gesture control device 22 may include the detection of unexpected gestures (e.g., gestures identifiably by gesture control device 22 but not associated with the particular mode in which gesture control device 22 is operating) or any other loss of system confidence in positive gesture detection. Such loss of confidence may be the result of the detection of multiple different gestures at the same time (e.g., inability to distinguish between gestures) or a detected error with one or more sensors that detect gestures.

Responsive to detecting the unexpected object, gesture control device 22 may be configured to exit, or suspend, the gesture control mode to prevent detection of erroneous gesture input due to the unexpected object. Once the gesture control mode is exited, gesture control device 22 may require an indicator gesture input or another user input that requests re-entry of gesture control mode before gesture control device 22 will re-enter the gesture control mode. Alternatively, gesture control device 22 may automatically unsuspend, or re-enter, a gesture control mode after receiving an indication to unsuspend the gesture control mode. For example, gesture control device 22 may monitor the field input data for changes to the unexpected object and unsuspend, or re-enter, the gesture control mode in response to determining that the unexpected object is no longer present in the envelope. In some examples, gesture control device 22 may re-enter the gesture control mode after a predetermined gesture control timeout has lapsed and, if an unexpected object remains in the envelope, the gesture control device 22 may again suspend the gesture control mode.

In some examples, gesture control device 22 may exit the gesture control mode in response to receiving user input requesting that the gesture control mode be terminated. For example, gesture control device 22 may be configured to receive field input data or gesture input and determine that the third gesture input is a termination gesture input (e.g., a gesture input that requests termination of the gesture control mode). Responsive to determining that the gesture input is a termination gesture input, gesture control device 22 may exit the gesture control mode. In some examples, the termination gesture input may include a gesture different than a control gesture and an indicator gesture. In other words, the termination gesture input may be specific to termination of the gesture control mode.

As discussed herein, gesture control device 22 may be controlled to exit, or terminate, the gesture control mode used to enable control gesture input control of one or more actions related to the medical procedure. Gesture control device 22 may be configured to receive an indication to enter the gesture control mode during which gesture control device 22 is configured to control one or more actions related to the medical procedure. In indication may be an indicator gesture input, another user input, entering a new step in a medical procedure, or some other request to enter the gesture control mode. Responsive to receiving the indication, gesture control device 22 enters the gesture control mode.

During the gesture control mode, gesture control device 22 may monitor field input data received during the gesture control mode for one or more control gesture inputs. The one or more control gesture inputs may be a request for gesture control device 22 to control one or more actions related to the medical procedure, such as operating a surgical device or adjusting a parameter value that at least partially defines therapy delivered by an implantable medical device. Gesture control device 22 may determine, during the gesture control mode, to exit the gesture control mode and, responsive to determining to exit the gesture control mode, gesture control device 22 may exit the gesture control mode. Exiting, or terminating, the gesture control mode may disable gesture input control of the one or more actions related to the medical procedure. In other words, gesture control device 22 may be configured to accept gesture input control of an action of the medical procedure only during the gesture control mode to mitigate error from inadvertent gesture input, for example.

Gesture control device 22 may be configured to exit the gesture control mode based on the progress of the medical device. For example, gesture control device 22 may be configured to monitor a progress of the medical procedure, where the medical procedure includes a plurality of steps and, for one step of the plurality of steps, gesture control device 22 is configured to accept gesture input controlling one or more actions related to the medical procedure during the one step. Gesture control device 22 may determine, based on monitoring the medical procedure progress, that the one step of the medical procedure has been completed, and, responsive to determining that the one step has been completed, gesture control device 22 may exit the gesture control mode. For example, gesture control device 22 may monitor the medical procedure progress via user input identifying when the procedure moves to the next step, user input completing a step, and/or actions performed by one or more devices in communication with gesture control device 22.

Gesture control device 22 may also monitor the progress of the medical procedure for multiple steps for which gesture input can be used to control an action. Gesture control device 22 may accept one or more gesture inputs of a first plurality of gesture inputs during the first step and determine that the medical procedure has entered a second step of the medical procedure. The first and second steps may not be sequential steps of the medical procedure. Responsive to the determination that the medical procedure has entered the second step of the medical procedure, gesture control device 22 may enter the gesture control mode and accept one or more gesture inputs of a second plurality of gesture inputs during the second step. The second plurality of gesture inputs may be different than the first plurality of gesture inputs such that different sets of gesture inputs are used to control actions in the respective steps. Gesture control device 22 may determine that the second step of the medical procedure has been completed and, responsive to determining that the second step has been completed, exit the gesture control mode for the second step.

In other examples, gesture control device 22 may use other techniques for determining when to exit the gesture control mode. For example, gesture control device 22 may exit the gesture control mode after a predetermined gesture control timeout has lapsed from when the gesture control mode started. Predetermined gesture control timeouts may be different and specific to respective steps within the medical procedure. For example, gesture control device 22 may track a first gesture control timeout specific to a first step of the medical procedure and a second gesture control timeout specific to a second step at a different portion of the medical procedure. The predetermined specific gesture control timeouts may be pre-selected for a particular step of the medical procedure such that the gesture control mode is active only for the time necessary to control the actions associated with the respective step of the medical procedure.

In another example, and as described herein, gesture control device 22 may suspend or terminate the gesture control mode in response to detecting an unexpected object within the envelope for detecting gesture input. For example, gesture control device 22 may receive first field input data during the gesture control mode, detect, from the first field input data, an unexpected object in an envelope within which gesture input can be sensed, and, responsive to detecting the unexpected object, suspend the gesture control mode to prevent detection of erroneous gesture input due to the unexpected object. Gesture control device 22 may also receive second field input data during the suspension of the gesture control mode, detect, from the second field input data, that the unexpected object is no longer in the envelope, and, responsive to detecting that the unexpected object is no longer in the envelope, re-enter the gesture control mode. Alternatively, gesture control device 22 may simply terminate the gesture control mode in response to detecting the unexpected object.

Gesture control device 22 may also receive a confirmation gesture input to confirm that a control gesture input was to be received by the gesture control device. For example, gesture control device 22 may be configured to receive, during the gesture control mode, an indication of one or more control gesture inputs requesting gesture control device 22 to control one or more actions related to the medical procedure. Gesture control device 22 may also receive, during the gesture control mode, a confirmation gesture input confirming that the one or more control gesture inputs were to be detected. Responsive to receiving both the one or more control gesture inputs and the confirmation gesture confirmation input, gesture control device 22 may control, based on the one or more control gesture inputs, the one or more actions related to the medical procedure. In this manner, the control gesture input may be used to minimize actions based on inadvertent gesture control inputs because a confirmation gesture input may be required. In some examples, the confirmation gesture input may be different from any control gesture inputs gesture control device 22 may use to control actions related to the medical procedure. Confirmation gesture input may generally be as distinct from control gesture inputs as possible (e.g., use of a different number of hands, stationary vs. motion gestures, or other dissimilar gesture inputs). In some examples, the confirmation gesture input may require a specific combination of other gestures to minimize the possibility that a confirmation gesture input is inadvertently detected.

Gesture control device 22 may be configured to receive and detect different gesture inputs in different orders. For example, gesture control device 22 may require that an indicator gesture input for entering the gesture control mode is received prior to any control gesture input or that control gesture input is received prior to any confirmation gesture input. Alternatively, gesture control device 22 may be configured to receive different gesture inputs simultaneously. For example, gesture control device 22 may be configured to detect both an indicator gesture input for entering the gesture control mode at the same time as a control gesture input and, subsequent to receiving both inputs, control an action associated with the medical procedure. Similarly, gesture control device 22 may be configured to detect a control gesture input simultaneously with a confirmation gesture input. For example, user 14 may make a control gesture with hand 16A at the same time that user 14 makes a confirmation gesture with hand 16B to confirm that the control gesture is intended.

Although gesture control device 22 is described as an external device that houses one or more processors that determine the gesture input and control one or more action associated with the medical procedure based on the gesture input, one or more other devices may perform the features of gesture control device 22. For example, a networked server, a medical device programmer, or an implantable medical device (e.g., IMD 18) may be configured to house the one or more processors configured to perform at least some of the features attributed to gesture control device 22.

As described herein, gesture input is generally described as requests to adjust a therapy, control a surgical process, or otherwise affect a treatment of patient 12. In other examples, gesture input may also be used to control a monitoring and/or diagnostic process for patient 12. In some examples, gesture control device 22 may be configured to control the flow of information between medical devices or from one medical device to another device. For example, gesture control device 22 may be configured to move patient data from a diagnostic device (e.g., a heart-rate monitor or fluoroscope) to a networked device that manages the electronic medical record (EMR) of patient 12. In another example, gesture control device 22 may be configured to associate a multiple medical devices (e.g., connect a fluoroscope, computed-tomography scanner, and a patient programmer that controls IMD 18) in response to detecting the appropriate gesture input from user 14. This association of multiple medical devices using gesture input may allow user 14 to optimize therapy parameter selection based on the output of one or more of the associated medical devices. In this manner, gesture control of multiple devices and the flow of patient data immediately during interaction with patient 12 may improve patient safety, procedural outcomes, and codification of patient treatment.

Figure 2:
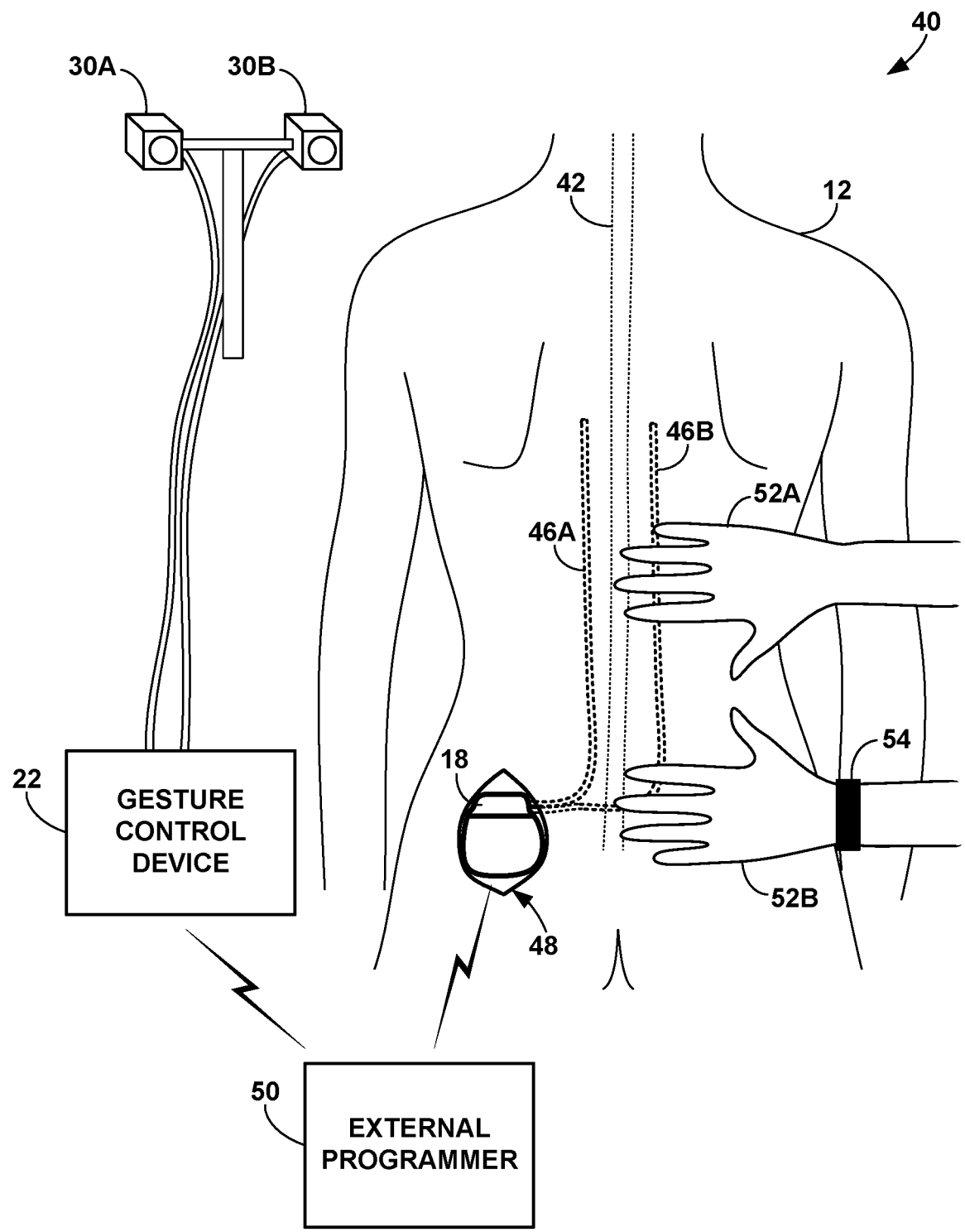
FIG. 2 is a conceptual diagram illustrating an example system that includes a gesture control device and implantable medical device that detect gesture input from a user for controlling one or more actions of a medical procedure.

FIG. 2 is a conceptual diagram illustrating example system 40 that includes gesture control device 22 and IMD 18 that detect gesture input from a user for controlling one or more actions of a medical procedure. System 40 may be similar to system 10 described in FIG. 1. For example, systems 10 and 40 include sensors 30A and 30B in communication with gesture control device 22, patient 12, and IMD 18. However, system 40 may incorporate detection capabilities from IMD 18 when determining a gesture control input and/or confirming that the received gesture control input is from the intended user (e.g., a clinician working with patient 12). IMD 18 may be configured to deliver spinal cord stimulation (SCS) to a patient 12. In other examples, IMD 18 may additionally or alternatively be configured to provide peripheral nerve field stimulation (PNFS), occipital nerve stimulation, sacral nerve stimulation (SNS), pelvic floor stimulation, or any other electrical stimulation therapy. Alternatively, or additionally, IMD 18 may be configured to deliver a different therapy (e.g., drug therapy), monitor one or more physiological parameters of patient 12, or provide any other service for patient 12.

As shown in FIG. 2, system 40 includes an IMD 18 and external programmer 50 shown in conjunction with a patient 12, who is ordinarily a human patient. In the example of FIG. 2, IMD 18 is an implantable electrical stimulator that delivers neurostimulation therapy to patient 12, e.g., for relief of chronic pain or other symptoms such as abnormal movements. Generally IMD 18 may be a chronic electrical stimulator that remains implanted within patient 12 for weeks, months, or even years. In the example of FIG. 2, IMD 18 and leads 46A and 46B (collectively "leads 46") may be directed to delivering SCS therapy. In other examples, IMD 18 may be a temporary, or trial, stimulator used to screen or evaluate the efficacy of electrical stimulation for chronic therapy. IMD 18 may be implanted in a subcutaneous tissue pocket, within one or more layers of muscle, or other internal location. IMD 18 may be coupled to leads 46, but fewer or greater numbers of leads may be used in other examples.

Electrical stimulation energy, which may be constant current or constant voltage based pulses, for example, is delivered from IMD 18 to one or more targeted locations within patient 12 via one or more electrodes (not shown) carried by each of respective leads 46. The parameters for a program that controls delivery of stimulation energy by IMD 18 may include information identifying which electrodes have been selected for delivery of stimulation according to a stimulation program, the combination of the selected electrodes, and the polarities of the selected electrodes, i.e., the electrode configuration for the program, and voltage or current amplitude, pulse frequency (or pulse rate), pulse shape, and pulse width of stimulation delivered by the electrodes. Electrical stimulation may be delivered in the form of stimulation pulses or continuous waveforms, for example.

In the example of FIG. 2, leads 46 are implanted and disposed within patient 12. Leads 46 are tunneled through tissue of patient 12 from along spinal cord 42 to a subcutaneous tissue pocket or other internal location where IMD 18 is disposed (e.g., within the pocket exposed by skin opening 48. Although leads 46 may each be a continuous lead, one or both of leads 46 may include a lead extension or other segments that may aid in implantation or positioning of leads 46. In addition, proximal ends of leads 46 may include a connector (not shown) that electrically couples to a header of IMD 18. In addition to leads 46, additional leads may be implanted and coupled to IMD 18 or another implantable medical device. In some examples, one or more leadless IMDs may be implanted within patient 12 and in communication with IMD 18 and/or external programmer 50.

Leads 46 may each carry one or more electrodes that are placed adjacent to the target tissue, e.g., spinal cord 42 for spinal cord stimulation (SCS) therapy. One or more electrodes may be disposed at or near a distal tip of leads 46 and/or at other positions at intermediate points along leads 46, for example. Electrodes of leads 46 are configured to transfer electrical stimulation generated by an electrical stimulation generator (or multiple generators) in IMD 18 to tissue of patient 12. The electrodes may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy.

IMD 18 may be configured to deliver electrical stimulation therapy to patient 12 via selected combinations of electrodes carried by one or more of leads 46. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 2, the target tissue for electrical stimulation delivered via leads 46 is tissue proximate spinal cord 42 (e.g., one or more target locations of the dorsal columns or one or more dorsal roots that branch from spinal cord 42). Leads 46 may be introduced into spinal cord 42 via any suitable region, such as the thoracic, cervical or lumbar regions. Stimulation of dorsal columns, dorsal roots, and/or peripheral nerves (e.g., afferent nerves) may, for example, prevent pain signals from traveling through spinal cord 42 and to the brain of the patient. Patient 12 may perceive the interruption of pain signals as a reduction in pain and, therefore, efficacious therapy results. For treatment of other disorders, leads 46 may be introduced at any exterior location of patient 12.

Although leads 46 is described as generally delivering or transmitting electrical stimulation signals, lead 46 may additionally transmit electrical signals from patient 12 to IMD 18 for monitoring. For example, IMD 18 may utilize detected nerve impulses to diagnose the condition of patient 12 or adjust the delivered stimulation therapy. Leads 46 may thus transmit electrical signals to and from patient 12. One or more of leads 46 may carry other sensors such as accelerometers, ultrasound sensors or transducers, and temperature sensors.

A user, such as a clinician or patient 12, may interact with a user interface of an external programmer 50 to program IMD 18, during implantation of IMD 18 and/or after implantation during use of IMD 18. Programming of IMD 18 may refer generally to the generation and transfer of commands, programs, or other information to control the operation of IMD 18. In this manner, IMD 18 may receive the transferred commands and programs from programmer 50 to control stimulation therapy. For example, external programmer 50 may transmit programs, parameter adjustments, program selections, group selections, user input, or other information to control the operation of IMD 18, e.g., by wireless telemetry or wired connection. As described herein, information may be transmitted between external programmer 50 and IMD 18. Therefore, IMD 18 and programmer 50 may communicate via wireless communication using any techniques known in the art. Examples of communication techniques may include, for example, radiofrequency (RF) telemetry and inductive coupling, but other techniques are also contemplated. In some examples, programmer 50 may include a communication head that may be placed proximate to the patient's body near the IMD 18 implant site in order to improve the quality or security of communication between IMD 18 and programmer 50. Communication between programmer 50 and IMD 18 may occur during power transmission or separate from power transmission.

External programmer 50 wirelessly communicates with IMD 18 as needed to provide or retrieve therapy information. Programmer 50 is an external computing device that the user, e.g., a clinician and/or patient 12, may use to communicate with IMD 18. For example, programmer 50 may be a clinician programmer that the clinician uses to communicate with IMD 18 and program one or more therapy programs for IMD 18. Alternatively, programmer 50 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 18.

When programmer 50 is configured for use by the clinician, programmer 50 may be used to transmit initial programming information to IMD 18. For example, the clinician may store therapy programs within IMD 18 with the aid of programmer 50. Programmer 50 may assist the clinician in the creation/identification of therapy programs by providing a methodical system for identifying potentially beneficial therapy parameter values. Programmer 50 may also, or alternatively, be configured for use by patient 12. When configured as a patient programmer, programmer 50 may have limited functionality (compared to a clinician programmer) in order to prevent patient 12 from altering critical functions of IMD 18 or applications that may be detrimental to patient 12. In this manner, programmer 50 may only allow patient 12 to adjust values for certain therapy parameters or set an available range of values for a particular therapy parameter.

Programmer 50 may provide information to the clinician and/or patient 12. For example, programmer 50 may present an indication to patient 12 when therapy is being delivered, when patient 12 input has triggered a change in therapy or when the power source within programmer 50 or IMD 18 needs to be replaced or recharged. For example, programmer 50 may include an alert LED, may flash a message to patient 12 via a programmer display, or generate an audible sound or somatosensory cue to confirm patient input was received, e.g., to indicate a patient state or to manually modify a therapy parameter. In addition, programmer 50 may present information to patient 12 and/or the clinician during implantation of IMD 18 and/or programming of IMD 18.

In addition to monitoring and/or providing therapy to patient 12 via IMD 18, system 40 may include additional devices configured to detect gesture input and control one or more actions of a medical procedure based on the detected gesture input. System 40 may thus include a gesture interface that incorporates data obtained by IMD 18. Similar to system 10 of FIG. 1, sensors 30 (e.g., camera-based sensors) may be positioned in such a manner to capture the movements of one or more anatomical regions of patient 12, such as one or both of hands 52. Sensors 30 may also be configured to detect a wearable device for detection of gestures, such as gesture device 54. Sensors 30 may be positioned to detect hands 52A, 52B within an envelope of space that may or may not include a portion of patient 12. However, the envelope may be selected such that hands 52 must be placed within the envelope adjacent to patient 12 to reduce the possibility that unintended users movements are detected as unintended gesture inputs.

Gesture control device 22 may be in communication with sensors 30 and/or control the operation of sensors 30. For example, gesture control device 22 may receive field input data (e.g., raw video data) or gesture inputs (e.g., processed raw video data) from sensors 30. As discussed in FIG. 1, gesture control device 22 may determine various gesture inputs based on the information received from sensors 30 and control, based on the gesture input received, one or more actions of a medical procedure. For example, gesture control device 22 may control an implantation device that assists a clinician to insert leads 46 into patient 12, an imaging device that assists the clinician in determining the location of the implanted lead within patient 12, or even external programmer 50 and/or IMD 18 in programming initial parameter values during the implantation process for leads 46 and IMD 18.

However, in the example of FIG. 2, gesture control device may receive additional information regarding gesture input to ensure the anticipated user has provided the gesture and/or confirm that the gesture input detected by sensors 30 was correct and intended by the user. For example, IMD 18 may generate gesture information and transmit the information to gesture control device 22 via external programmer 50. Since external programmer 50 may be in communication with gesture control device 22 and IMD 18, IMD 18 may transmit gesture information to external programmer 50, and external programmer 50 may then transmit the gesture information to gesture control device 22. The gesture information may be unprocessed by external programmer 50, or external programmer 50 may process the signals from IMD 18 and generate the gesture information sent to gesture control device 22.

IMD 18 may be configured to detect gestures or the presence of hands 52A and 52B (collectively "hands 52") and/or gesture device 54. For example, leads 46 may transmit changes in electrical fields caused by the presence of hands 52 of a user (e.g., user 14), the presence of wearable gesture device 54, or changes in tissue from patient 12 to IMD 18. These changes may be indicative of the presence of one or both of hands 52 to detect gesture input and/or confirm that the gesture input was detected by an expected user in the vicinity of patient 12. One or more of leads 46 may also include one or more sensors configured to detect the presence of hands 52 and/or gesture device 54. In this manner, leads 46 may carry electrodes and/or other types of sensors configured to monitor patient 12, provide therapy to patient 12, and/or detect gestures from the user and/or patient 12.

Using the signals received from leads 46 and/or any other sensors, IMD 18 may generate gesture information representative of the presence and/or motions of hands 52 and transmit the gesture information to external programmer 50 en route to gesture control device 22. IMD 18 may detect gestures and/or generate gesture information periodically, in response to specific steps in a medical procedure, or in response to a request received from gesture control device 22. For example, gesture control device 22 may determine that a gesture control mode has been entered and transmit a request to IMD 18 to begin transmitting gesture information back to gesture control device 22 for the duration of the gesture control mode. Although IMD 18 may transmit gesture information to gesture control device 22 via external programmer 50, IMD 18 may directly transmit gesture information to gesture control device 22 in other examples. In alternative examples, external programmer 50 may perform the functions of gesture control device 22 and control medical devices based on the gesture input received from sensors 30 and/or IMD 18.

Gesture control device 22 may control actions of a medical procedure according to field input data received from sensors 30 and gesture information received from IMD 18. For example, gesture control device 22 may determine gesture input based on both the information from sensors 30 and IMD 18. In some examples, gesture control device 22 may receive the gesture input from sensors 30 (e.g., field input data) and confirm that the gesture input was from gestures made by one or more hands 52 close to patient 12. In other words, IMD 18 may monitor a change in electrical field from leads 46 or receive data indicative of the presence of hands 52 that indicates the gestures were made by the clinician working with patient 12. Gesture control device 22 may thus use the gesture information from IMD 18 as a confirmation that the gesture input was not inadvertent or from an unintended user. In some examples, gesture control device 22 may compare the field input data from sensors 30 to the gesture information from IMD 18 to determine if the field input data correlates with the gesture information. Although the field input data may be more detailed (e.g., fine resolution) regarding the conformation and/or movements of hands 52, the gesture information from IMD 18 may indicate coarse resolution regarding the movement or presence of hands 52. Therefore, the gestures detected from the field input data from sensors 30 may correlate to the general coarse representation of the gestures detected by IMD 18. Gesture control device 22 may thus use the gesture information from IMD 18 to confirm or otherwise increase the probability that the gesture input is accurate and from the intended user. If gesture control device 22 does not determine that the field input data correlates with gesture information from IMD 18, gesture control device 22 may discard any gesture input from the field input data or otherwise withhold any action based on the field input data because the gesture information did not confirm the gesture input.

In this manner, field input data from sensors external from patient 12 may be particularly useful to correlate gestures provided in spatial relation to a specific location of patient anatomy or medical components implanted within patient 12. This correlation may be used by gesture control device 22 to change an aspect of therapy at that particular location of the patient. For example, IMD 18 may detect the location of one or more hands 52 with respect to an anatomical landmark and/or component associated with IMD 18 (e.g., one or more electrodes of a lead connected with IMD 18), and field input data from sensors 30 may be used to detect gesture input at that location. The gesture input may request a change to a stimulation parameter (e.g., increase or decrease stimulation intensity, pulse width and/or pulse rate and/or change the selected electrode configuration used to deliver stimulation therapy) or indicate a certain beneficial effect or side effect of therapy at that location of patient anatomy. IMD 18 and/or gesture control device 22 may thus associate the change in therapy or other information from the gesture input to the detected anatomical and/or component position and generate an instruction related to therapy. For example, the instruction may be a change to a therapy parameter at that identified location of anatomy or identified medical component or a notation regarding the therapy that is associated to the anatomical location. The instruction or notation may be stored by IMD 18 and/or another device of system 10. In this manner, system 10 may receive instructions based on both the field input data from sensors 30 and gesture information from IMD 18.

In some examples, IMD 18 may generate the gesture information from the location of gesture device 54. The clinician may wear gesture device 54 to identify one or both of hands 52 as the hands of the clinician. IMD 18 may include a transceiver or other communication device that detects when gesture device 54 is within a predetermined distance of IMD 18. Gesture device 54 may include a similar transponder or circuitry to allow IMD 18 and gesture device 54 to determine when the gesture device is within the predetermined distance of IMD 18. An example transponder or communication protocol may include Bluetooth protocol, near-field communication protocol, or any other one-way or two-way communication protocol. In other examples, gesture device 54 may detect that it is within a predetermined distance from IMD 18 and/or leads 46 and transmit that information to external programmer 50 and/or gesture control device 22 for use by gesture control device in confirming the detected gesture input. In some examples, gesture device 54 may include a motion sensing device (e.g., accelerometer and/or gyroscope) that provide additional information regarding the movement of hand 52.

Gesture device 54 may be constructed in the form of a band, bracelet, ring, attachable patch, or even as part of a glove worn by one or both of hands 52. Gesture device 54 may be a passive device that is only detectable by another device (e.g., a device that reflects light, alters an electric field, or a passive near-field communication circuit). In this manner, gesture device 54 may be a device configured to improve the efficiency or accuracy of external components (e.g., sensors 30) or implanted components (e.g., IMD 18) for detection of gesture inputs (e.g., reflective elements for modalities such as optical detection or resonant circuits for acoustic systems). Alternatively, gesture device 54 may include circuitry that provides active communication with another device, such as IMD 18, external programmer 50, and/or gesture control device 22. Although gesture device 54 is shown on only hand 52B, another gesture device 54 may be worn on hand 52A, or a plurality of gesture devices may be worn on respective fingers of one or both of hands 52.

In configurations where gesture information from IMD 18 only provides a coarse representation of the presence of hands 52, the gesture information may only be used as a confirmation of gesture input (e.g., used in conjunction with more fine resolution data such as field input data from sensors 30). However, coarse gesture information and/or more fine resolution gesture information from IMD 18 may be used alone by gesture control device 22 to determine gesture input for control of medical procedure actions. In other words, field input data from sensors 30 may not be necessary in some circumstances. For example, IMD 18 may detect positions and/or movements of one or both of hands 52 with respect to IMD 18 and/or electrodes or other sensors carried by leads 46. IMD 18 may generate this gesture information and transmit the gesture information to external programmer 50 and/or gesture control device 22 to allow gesture control device 22 to control an action related to the medical procedure. Alternatively, IMD 18 may directly use this gesture information to adjust one or more parameter values that defines therapy delivered by IMD 18 and/or send the gesture information to external programmer 50. For example, IMD 18 may be configured to detect relative hand movement up or down an implanted lead to provide gesture information that correlates to an increase or decrease, respectively, of stimulation intensity. However, the detection of absolute hand position with respect to one or more leads or other implanted components may also be used to provide gesture information. In any example, IMD 18 may generate gesture information that is itself sufficient to detect at least some types of gesture input from a user.

Gesture information from IMD 18 may be particularly useful for gesture control of IMD 18 since only the clinician positioned near patient 12 will be control over IMD 18. In addition, when IMD 18 is being implanted, the clinician may be near patient 12 and it may be desirable not to physically touch any other devices during the procedure. For example, skin opening 48 may be susceptible to infection due to lead 46 and IMD 18 implantation. During this time, gesture input control of one or more aspects of the medical procedure may reduce the risk of infection and/or contamination of handheld devices. Moreover, IMD 18 detection of hands 52 may cause gesture control device 22 to switch control of devices using gesture input. For example, gesture control device 22 may control a surgical device using gestures from hands 52. In response to receiving gesture information from IMD 18 that indicates the presence of hands 52 near IMD 18, gesture control device 22 may switch gesture input control from the surgical device to control of IMD 18 (e.g., adjusting one or more parameters that defines the operation of IMD 18).

In some examples, gesture information from IMD 18 may be used as an indicator gesture input and/or termination gesture input. For example, in response to receiving gesture information from IMD 18 that indicates hands 52 have been detected, gesture control device 22 may enter the gesture control mode for control of IMD 18 using field input data from sensors 30. Similarly, hands 52 no longer detected by the gesture information may be a termination gesture input that causes gesture control device 22 to exit the gesture control mode.

System 40 is generally described for use during implantation of IMD 18. However, IMD 18 may generate gesture information in other situations as well. For example, IMD 18 may be used by a gesture control device during a programming session for IMD 18 in a clinician's office. IMD 18 may generate gesture information during the programming session and transmit the gesture information to external programmer 50 or gesture control device 22 for facilitating gesture input control during the programming session.

Although IMD 18 is generally described in FIG. 2, techniques of this disclosure may also be applicable to external or partially external medical device in other examples. For example, IMD 18 may instead be configured as an external medical device coupled to one or more percutaneous medical leads or even externally attached leads or devices. The external medical device may be a chronic, temporary, or trial electrical stimulator. In addition, an external electrical stimulator may be used in addition to one or more IMDs 18 to deliver electrical stimulation described herein. External medical devices may similarly be configured to detect the presence of hands 52 and/or gesture device 54 to detect gesture input, assist in the detection of gesture input, and/or confirm the presence of hands 52 or gesture device 54 that aids the determination of gesture input by gesture control device 22.

Figure 3:
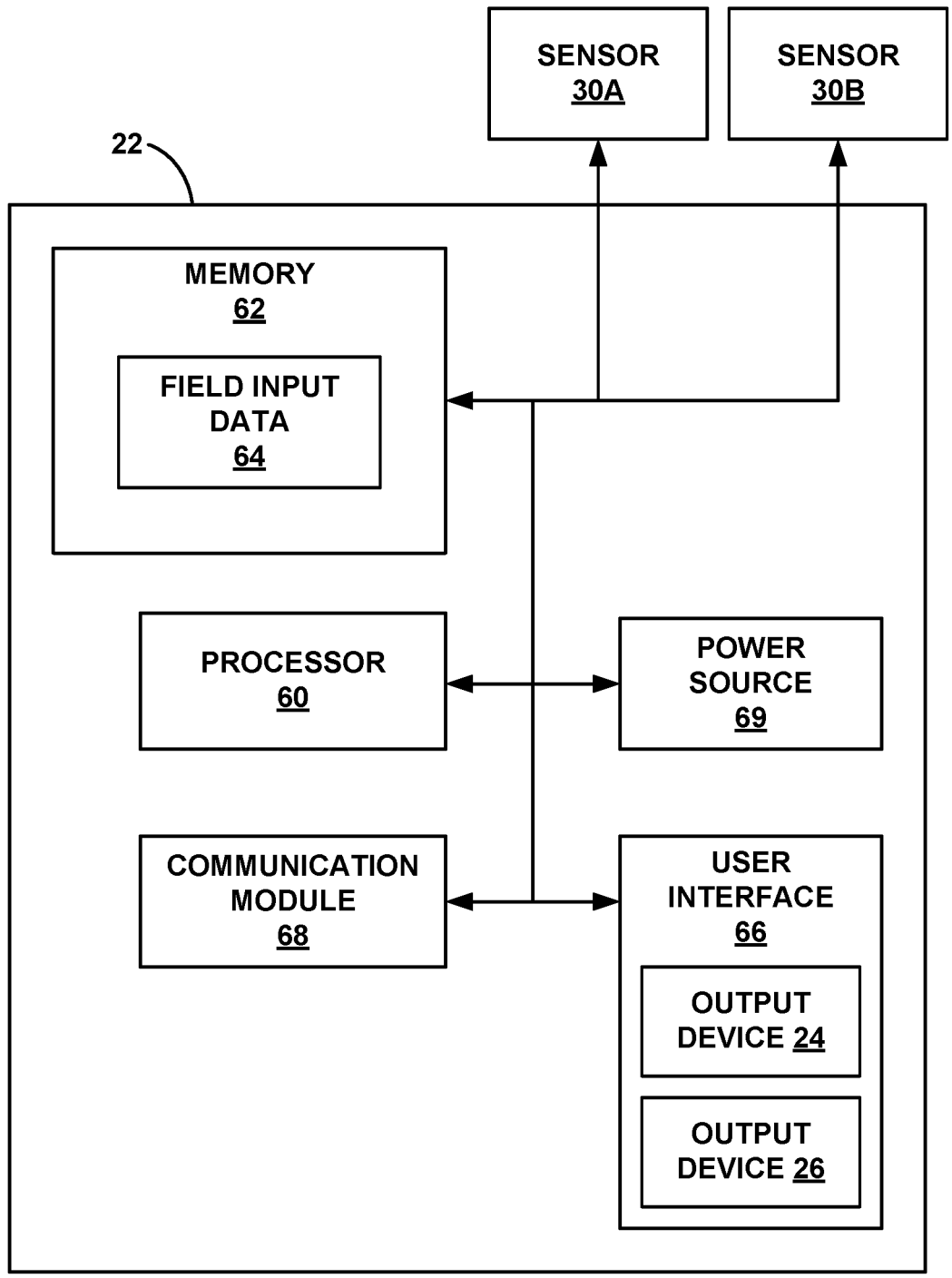
FIG. 3 is a block diagram of an example gesture control device of FIGS. 1 and 2.

FIG. 3 is a block diagram of example gesture control device 22 of FIGS. 1 and 2. FIG. 3 illustrates only one particular example of gesture control device 22, and many other example embodiments of gesture control device 22 may be used in other instances. For example, gesture control device 22 may include additional components and run multiple different applications. Gesture control device 22 may be configured to obtain and/or generate gesture input from sensors 30A and 30B. Gesture control device 22 may also generate commands for transmission to other devices for control during a medical procedure.

As shown in FIG. 3, gesture control device 22 may include processor 60, memory 62, user interface 66, communication module 68, and power source 69. Sensors 30 may be located separately from gesture control device 22 and in communication with gesture control device 22 and processor 60. In other examples, sensors 30 may be incorporated within gesture control device 22. Each of components 30A, 30B, 60, 62, 66, 68 and 69 may be interconnected (physically, communicatively, and/or operatively) for inter-component communications and functionality.

Processor 60, in one example, is configured to implement functionality and/or process instructions for execution, such as controlling sensors 30, receiving field input data 64, and determining gesture input. Field input data 64 may include the data received from sensors 30 and may be stored in memory 62 for temporary and/or long term storage. Processor 60 may also be configured to process instructions stored within memory 62. Processor 60 may also be configured to generate metadata or supplemental data (e.g., time stamps or any other related information) to field input data 64 and/or gesture inputs and store such data with the video frames as the field input data 64.

Memory 62, in one example, is configured to store information within gesture control device 22 during operation. Memory 62, in some examples, is described as a computer-readable storage medium. Memory 62 may also be described as a storage device or computer-readable storage device. In some examples, memory 62 is a temporary memory, meaning that a primary purpose of memory 62 is not long-term storage. However, memory 62 may also be described as non-transitory. Memory 62, in some examples, may be described as a volatile memory, meaning that memory 62 does not maintain stored contents when the computer is turned off. Examples of volatile memories include random access memories (RAM), dynamic random access memories (DRAM), static random access memories (SRAM), and other forms of volatile memories known in the art. In some examples, memory 62 is used to store program instructions for execution by processor 60.

Gesture control device 22, in some examples, also includes a communication module 68. Gesture control device 22, in one example, utilizes communication module 68 to communicate with other computing devices (e.g., networked server 106 of FIG. 7), programmers (e.g., programmer 50 of FIG. 2), sensors 30 in some examples, medical devices (e.g., IMD 18 and/or medical device 112), or more networks, such as network 110 shown in FIG. 7. In this manner, gesture control device 22 may transmit field input data 64 to other computing devices for analysis, receive gesture control information resulting from the field input data, and/or transmit control information to other medical devices to be controlled. Communication module 68 may be a network interface card, such as an Ethernet card or other wired interface. In other examples, communication module 68 may include an optical transceiver, a radio frequency transceiver, or any other type of device that can send and receive information. Other examples of such communication modules may include Bluetooth, 3G and WiFi radios in mobile computing devices as well as USB. In some examples, gesture control device 22 utilizes communication module 68 to wirelessly communicate with another computing device (e.g., external programmer 50 of IMD 18 of FIG. 2) or one or more networks.

Gesture control device 22, in one example, also includes one or more user interface 66. User interface 66 may include a touch-sensitive screen, mouse, a keyboard, a voice responsive system, camera, or any other type of device for detecting a command from a user. In one example, user interface 66 may include a touch-sensitive screen, sound card, a video graphics adapter card, or any other type of device for converting a signal into an appropriate form understandable to humans or machines. In addition, user interface 66 may include a speaker, a cathode ray tube (CRT) monitor, a liquid crystal display (LCD), or any other type of device that can generate intelligible output to a user. For example, user interface 66 includes output device 24 (e.g., a display device such as an LCD) and output device 26 (e.g., an audio device such as one or more speakers). User interface 66 may also include one or more input devices (e.g., a touch-sensitive screen, a pointing device, and/or a keyboard).

Gesture control device 22, in some examples, includes one or more power sources 69, which provide power to gesture control device 22. Generally, power source 69 may utilize power obtained from a wall receptacle or other alternating current source. However, in other examples, power source 69, may include one or more rechargeable or non-rechargeable batteries (e.g., constructed from nickel-cadmium, lithium-ion, or other suitable material). In other examples, power source 69 may be a power source capable of providing stored power or voltage from another power source.

Figure 4:
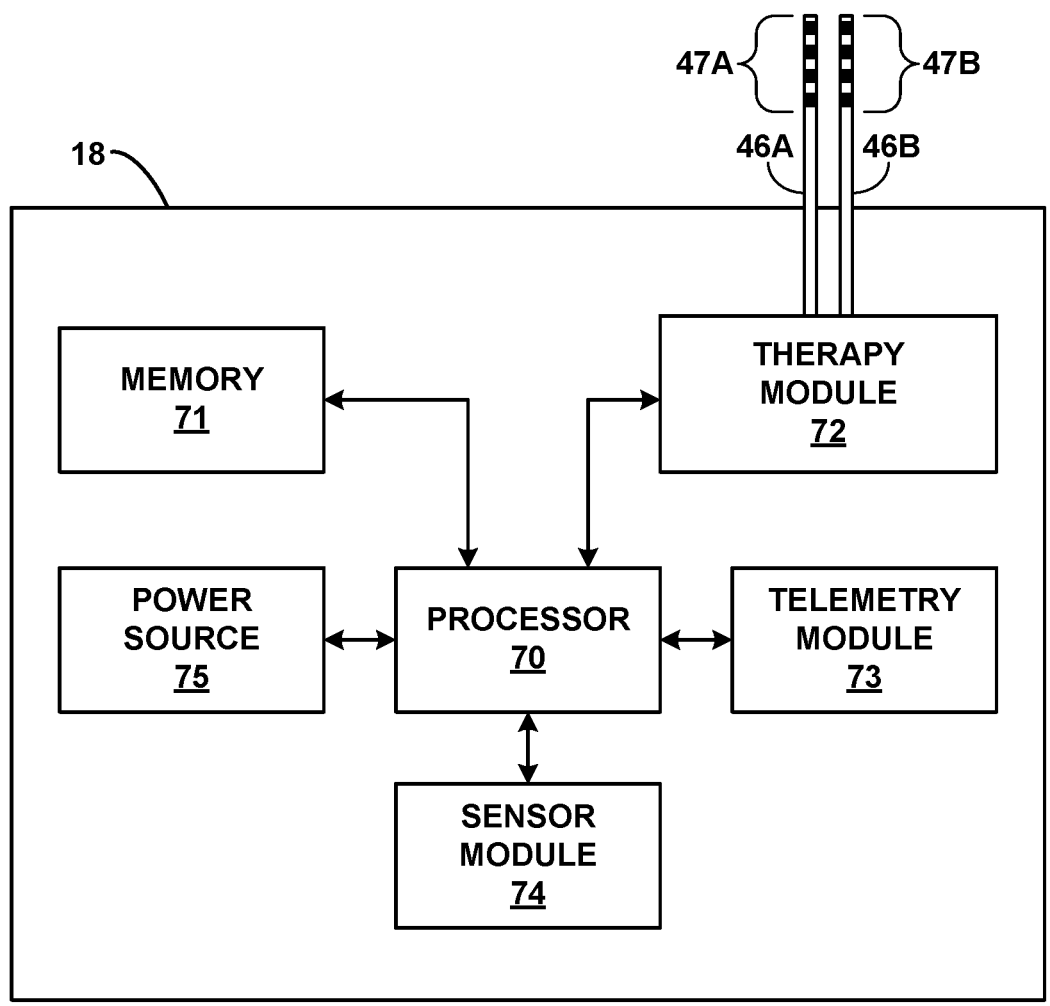
FIG. 4 is a block diagram of an example implantable medical device of FIGS. 1 and 2.

FIG. 4 is a block diagram of example IMD 18 of FIGS. 1 and 2. As shown in the example of FIG. 4, IMD 18 includes processor 70, therapy module 72, power source 75, memory 71, telemetry module 73, and sensor module 74. In other examples, IMD 18 may include a greater or fewer number of components. In general, IMD 18 may comprise any suitable arrangement of hardware, alone or in combination with software and/or firmware, to perform the various techniques described herein attributed to IMD 18 and processor 70. In various examples, IMD 18 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 18 also, in various examples, may include a memory 71, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 70, therapy module 72, and telemetry module 73 are described as separate modules, in some examples, processor 70, therapy module 72, and telemetry module 73 may be functionally integrated. In some examples, processor 70, therapy module 72, and telemetry module 73 may correspond to individual hardware units, such as ASICs, DSPs, FPGAs, or other hardware units.

Memory 71 (e.g., a storage device) may store therapy programs or other instructions that specify therapy parameter values for the therapy provided by therapy module 72 and IMD 18. In some examples, memory 71 may also store instructions for communication between IMD 18 and programmer 50, or any other instructions required to perform tasks attributed to IMD 18. Memory 71 may also store instructions for detecting gestures (e.g., the presence of a hand or gesture device as described in FIG. 2) and generating gesture information to aid in the error mitigation techniques described herein.

Generally, therapy module 72 may generate and deliver electrical stimulation under the control of processor 70. In some examples, processor 70 controls therapy module 72 by accessing memory 71 to selectively access and load at least one of the stimulation programs to therapy module 72. For example, in operation, processor 70 may access memory 71 to load one of the stimulation programs to therapy module 72. In such examples, relevant stimulation parameters may include a voltage amplitude, a current amplitude, a pulse frequency, a pulse width, a duty cycle, one or more spatial electrode movement patterns that define the combination of electrodes 47A carried by lead 46A or electrodes 47B carried by lead 46B that therapy module 72 uses to deliver the electrical stimulation signal. Although therapy module 72 may be configured to generate and deliver electrical stimulation therapy via one or more of electrodes 47A or 47B, a different therapy module may be configured to provide different therapy to patient 12, such as drug delivery therapy via a catheter. These and other therapies may be provided by IMD 18. Although four electrodes are shown as included in electrodes 47A and four electrodes are shown as included in electrodes 47B, fewer or greater number of electrodes may be provided in other examples.

An exemplary range of electrical stimulation parameters that may be used to deliver effective treatment for chronic pain, e.g., when applied to spinal cord 42, are listed below. While stimulation pulses are described, stimulation signals may be of any of a variety of forms such as sine waves or the like.

Pulse Frequency: between approximately 0.5 Hz and 10,000 Hz. In one example, pulse frequency may be between approximately 5 Hz and 250 Hz or between approximately 30 Hz and 130 Hz. In other examples, pulse frequency may be greater than 250 Hz or even greater than 1,000 Hz. Pulse frequencies greater than 1,000 Hz may be considered to be greater than the nerve firing potential of affected nerve fibers to inhibit nerve firing. However, in some examples, the pulse frequency may be between approximately 1,000 Hz and 10,000 Hz.

Amplitude: between approximately 0.1 volts and 50 volts, more preferably between approximately 0.5 volts and 20 volts, and still more preferably between approximately 1 volt and 10 volts. In other examples, a current amplitude may be defined as the biological load in the voltage that is delivered. For example, the range of current amplitude may be between approximately 0.1 milliamps (mA) and 50 mA. In other examples, current amplitude may be between approximately 1.0 mA and 10 mA.

Pulse Width: between about 10 microseconds and 5000 microseconds. In some examples, the pulse width may be between approximately 100 microseconds and 1000 microseconds or between approximately 180 microseconds and 450 microseconds. With higher frequency pulses, the pulse width may be smaller to accommodate the increased frequency. For example, the pulse width may be between approximately 10 microseconds and 50 microseconds.

Power source 75 may include one or more capacitors, batteries, or other energy storage devices. IMD 18 may thus also include an inductive coil and a recharge module (both not shown) configured to manage the recharging session for power source 75. Although inductive coupling may be used to recharge power source 75, other wireless energy transfer techniques may alternatively be used. Alternatively, power source 75 may not be rechargeable.

Processor 70 may also control the exchange of information with programmer 50, gesture device 54, and/or gesture control device 22 using telemetry module 73. Telemetry module 73 may be configured for wireless communication using radio frequency protocols or inductive communication protocols. Telemetry module 73 may include one or more antennas configured to communicate with programmer 50, for example. Processor 70 may transmit operational information and receive therapy programs or therapy parameter adjustments via telemetry module 73. Also, in some examples, IMD 18 may communicate with other implanted devices, such as stimulators, control devices, or sensors, via telemetry module 73. For example, telemetry module 73 may receive user input, spatial electrode movement patterns, or other commands from programmer 50. Accordingly, telemetry module 73 may send information to external programmer 50 on a continuous basis, at periodic intervals, or upon request from IMD 18 or programmer 50.

Sensor module 74 may be configured to detect position and/or motion of IMD 18, the presence of any hands of a user, or the presence of gesture device 54. For example, sensor module 74 may include one or more accelerometers, one or more gyroscopes, or any other movement detection devices. Sensor module 74 may additionally, or alternatively, include one or more ultrasound transducers, capacitive sensors, acoustic sensors, strain sensors, pressure sensors (e.g., on the surface of a housing of IMD 18), optical sensors, thermal sensors, or communication devices that may be configured to detect movement of hands or otherwise provide data related to gestures performed by a user. Any of all of these sensors may be used by sensor module 74 to detect gestures. IMD 18 may be configured to detect gesture input itself via the techniques discussed herein, without the use of information provided by other external sensors such as sensors 30 of system 10.

Although IMD 18 is described as providing spinal cord stimulation, IMD 18 may be configured to provide any number of other electrical stimulation therapies. For example, IMD 18 and leads 46 may be configured to provide deep brain stimulation, peripheral nerve stimulation, gastric stimulation, pelvic floor stimulation, or any other type of stimulation.

Figure 5:
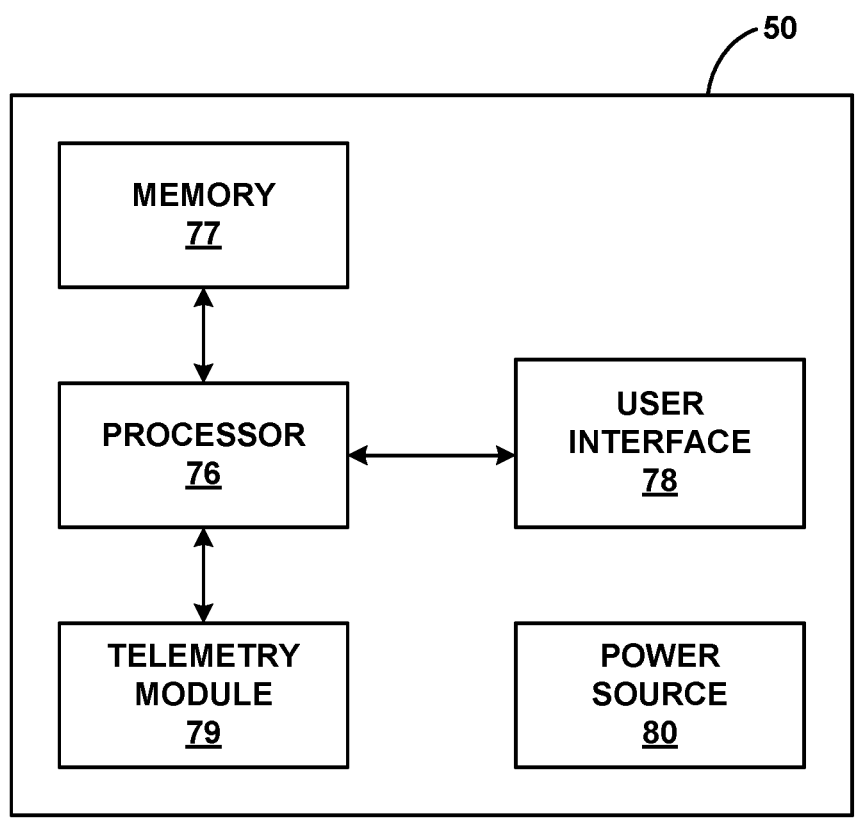
FIG. 5 is a block diagram of an example external programmer of FIG. 2.

FIG. 5 is a block diagram of example external programmer 50 of FIG. 2. Although programmer 50 may generally be described as a hand-held device, programmer 50 may be a larger portable device or a more stationary device. In addition, in other examples, programmer 50 may be included as part of an external charging device or include the functionality of an external charging device. As illustrated in FIG. 5, programmer 50 may include a processor 76, memory 77, user interface 78, telemetry module 79, and power source 80. Memory 77 may store instructions that, when executed by processor 76, cause processor 76 and external programmer 50 to provide the functionality ascribed to external programmer 50 throughout this disclosure. For example, processor 76 may be configured to transmit selected therapy parameter sets that at least partially define the operation of IMD 18 to IMD 18.

In general, programmer 50 comprises any suitable arrangement of hardware, alone or in combination with software and/or firmware, to perform the techniques attributed to programmer 50, and processor 76, user interface 78, and telemetry module 79 of programmer 50. In various examples, programmer 50 may include one or more processors, such as one or more microprocessors, DSPs, ASICs, FPGAs, or any other equivalent integrated or discrete logic circuitry, as well as any combinations of such components. Programmer 50 also, in various examples, may include a memory 77, such as RAM, ROM, PROM, EPROM, EEPROM, and flash memory (and a storage device such as a hard disk or a CD-ROM in some examples), comprising executable instructions for causing the one or more processors to perform the actions attributed to them. Moreover, although processor 76 and telemetry module 79 are described as separate modules, in some examples, processor 76 and telemetry module 79 are functionally integrated. In some examples, processor 76 and telemetry module 79 correspond to individual hardware units, such as ASICs, DSPs, FPGAs, or other hardware units.

Memory 77 (e.g., a storage device) may store instructions that, when executed by processor 76, cause processor 76 and programmer 50 to provide the functionality ascribed to programmer 50 throughout this disclosure. For example memory 77 may include instructions that cause processor 76 to obtain a parameter set from memory, select a spatial electrode movement pattern, or receive a user input and send a corresponding command to IMD 14, or instructions for any other functionality. In addition, memory 77 may include a plurality of programs, where each program includes a parameter set that defines stimulation therapy User interface 78 may include a button or keypad, lights, a speaker for voice commands, a display, such as a liquid crystal (LCD), light-emitting diode (LED), or organic light-emitting diode (OLED). In some examples the display may be a touch screen. User interface 78 may be configured to display any information related to the delivery of stimulation therapy, identified patient behaviors, sensed patient parameter values, patient behavior criteria, or any other such information. User interface 78 may also receive user input via user interface 78. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, or the input may request some other change to the delivery of electrical stimulation.

Telemetry module 79 may support wireless communication between IMD 14 and programmer 50 under the control of processor 76. Telemetry module 79 may also be configured to communicate with another computing device via wireless communication techniques, or direct communication through a wired connection. In some examples, telemetry module 79 may be substantially similar to telemetry module 73 of IMD 18 described herein, providing wireless communication via an RF or proximal inductive medium. In some examples, telemetry module 79 may include an antenna, which may take on a variety of forms, such as an internal or external antenna.

Examples of local wireless communication techniques that may be employed to facilitate communication between programmer 50 and other devices include RF communication according to the 802.11, Bluetooth specification sets, or other standard or proprietary telemetry protocols. In this manner, other external devices may be capable of communicating with programmer 50 without needing to establish a secure wireless connection. As described herein, telemetry module 79 may be configured to transmit a spatial electrode movement pattern or other stimulation parameter values to IMD 18 for delivery of stimulation therapy. Telemetry module 79 may utilize these wireless communication techniques to communicate with IMD 18 and/or other wireless communication protocols that provide a secure connection with IMD 18.

In some examples, external programmer 50 may be configured to perform the features attributed to gesture control device 22 described herein. For example, external programmer 50 may receive field input data from sensors 30 of FIG. 2 and determine gesture input from the field input data. In response to determining gesture input, processor 76 may determine corresponding actions such as adjustments to parameter values and transmit the adjustments to IMD 18.

Figure 6:
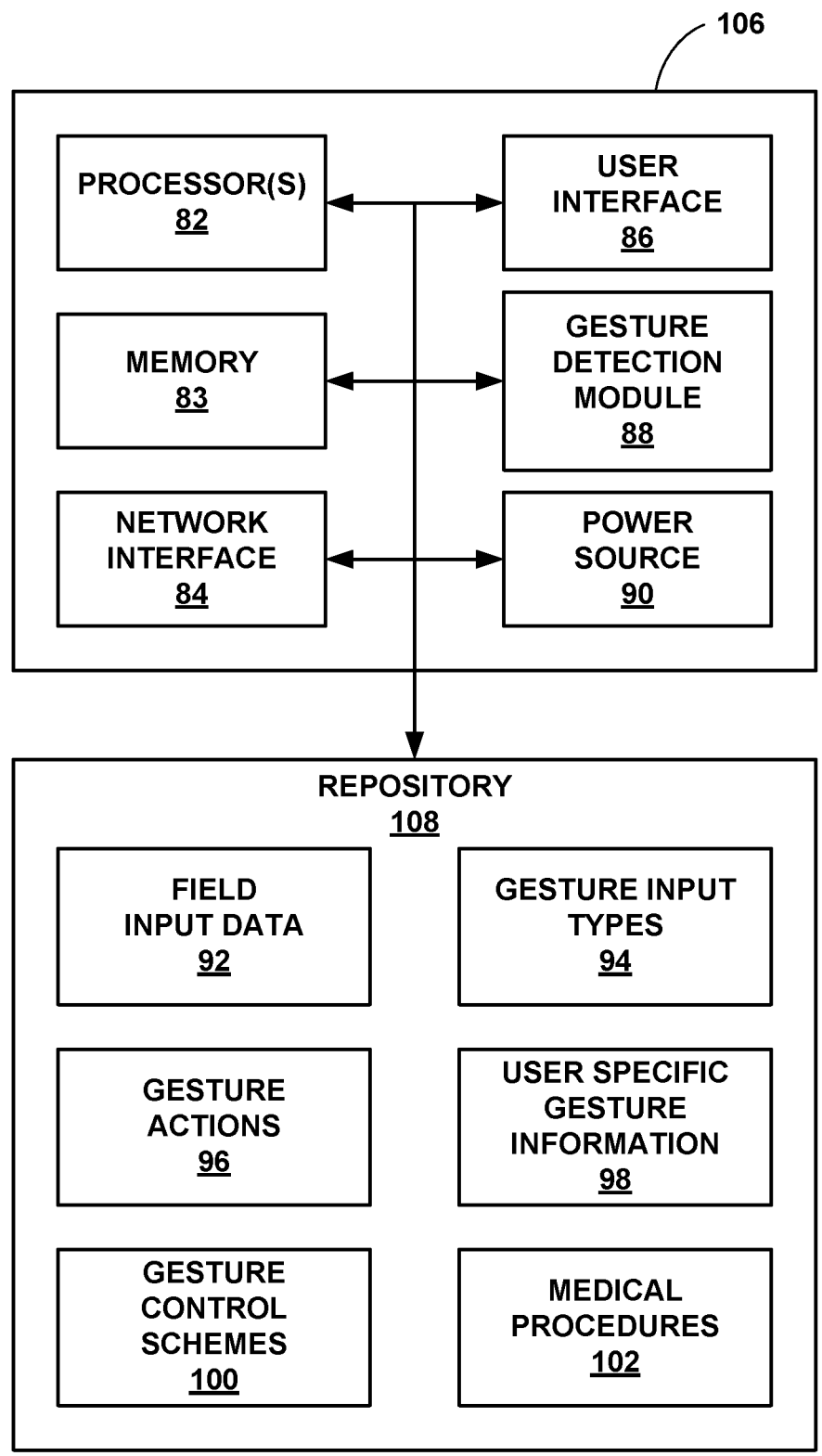
FIG. 6 is a block diagram of an example networked server.
Figure 7:
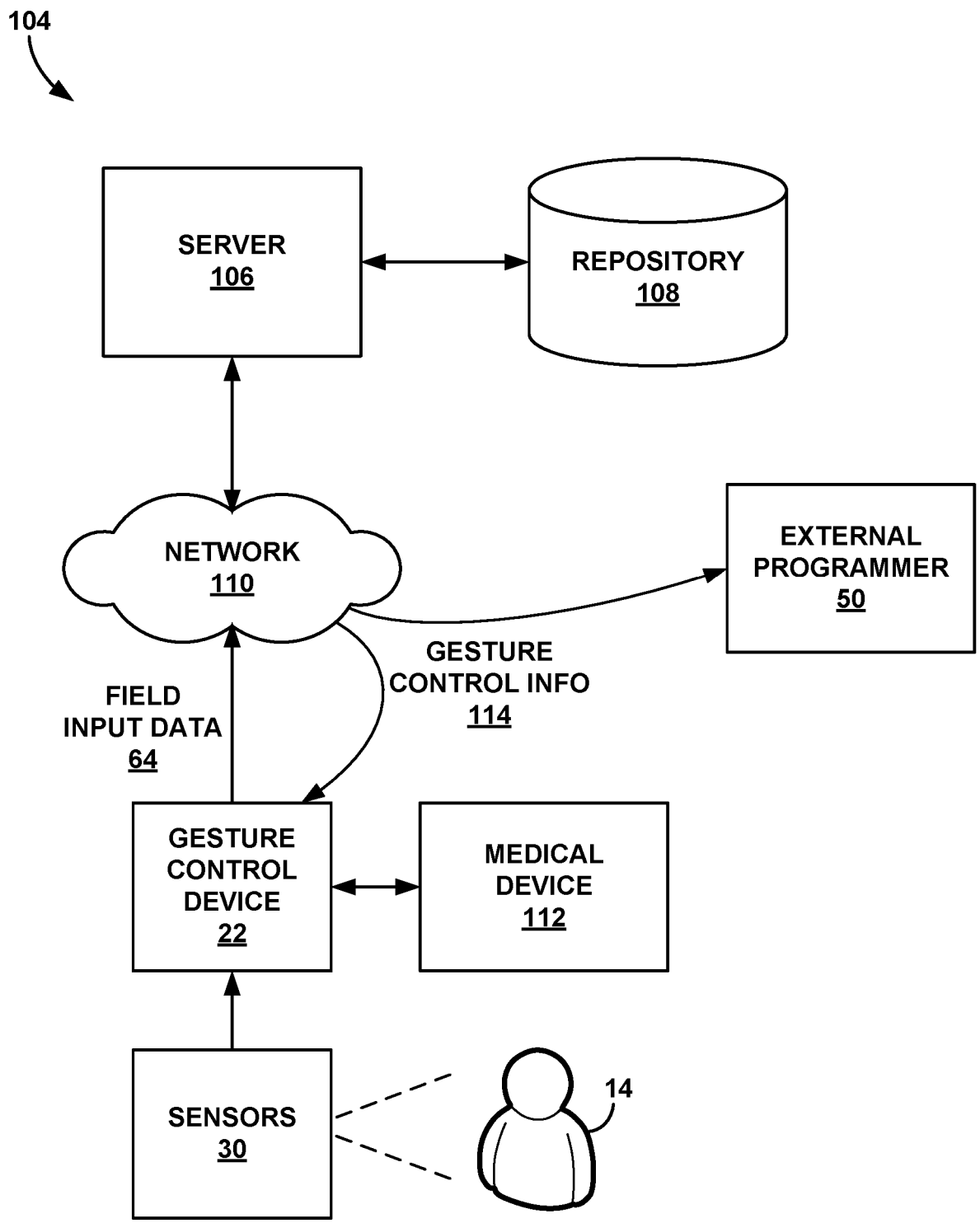
FIG. 7 is a conceptual diagram illustrating an example system that includes the networked server of FIG. 6 for determining gesture input based on received field input data.

FIG. 6 is a block diagram of an example networked server 106 and repository 46 of FIG. 7. FIG. 6 illustrates only one particular example of server 106, and many other example embodiments of server 106 may be used in other instances. For example, server 106 may include additional components and run multiple different applications. Although gesture control device 22 is generally described as determining gesture input and controlling one or more actions (e.g., one or more medical devices) for a medical procedure, server 106 may analyze field input data to determine gesture input and/or identify commands based on the received gesture input. Gesture control device 22 may be configured to transmit field input data, for example, to server 106 for analysis and processing to determine the gesture inputs received from a user. For example, server 106 may be configured to perform some or all of the processes described with respect to FIGS. 11-18.

As shown in the specific example of FIG. 6, server 106 may include and/or house one or more processors 82, memory 83, a network interface 84, user interface 86, gesture detection module 88, and power source 90. Server 106 may be in communication with repository 108, such that repository 108 is located external of server 106. In other examples, repository 108 may include one or more storage devices within an enclosure of server 106. Server 106 may also include an operating system, which may include modules and/or applications that are executable by processors 82 and server 106. Each of components 82, 83, 84, 86, 88, and 90 may be interconnected (physically, communicatively, and/or operatively) for inter-component communications.

Processors 82, in one example, are configured to implement functionality and/or process instructions for execution within server 106, such as determining gesture inputs from field input data and/or determining the controls corresponding to the received gesture input. Processors 82 may also, or alternatively, process gesture information from IMD 18 to determine whether or not a user's hand has provided a gesture or is otherwise present within an envelope near IMD 18 or leads 46. For example, processors 82 may be capable of processing instructions stored in memory 83 or instructions stored in repository 108. These instructions may define or otherwise control the operation of server 106. In some examples, gesture detection module 88 (which may include one or more dedicated processors) may be configured to analyze the field input data 92 (which may or may not be the same field input data 64 described in FIG. 3) and identify the gesture input received from the user within field input data 92.

Memory 83, in one example, is configured to store information within server 106 during operation. Memory 83, in some examples, is described as a computer-readable storage medium. Memory 83 may also be described as a storage device or computer-readable storage device. In some examples, memory 83 is a temporary memory, meaning that a primary purpose of memory 83 is not long-term storage. However, memory 83 may also be described as non-transitory. Memory 83, in some examples, may be described as a volatile memory, meaning that memory 83 does not maintain stored contents when the computer is turned off. Examples of volatile memories include random access memories (RAM), dynamic random access memories (DRAM), static random access memories (SRAM), and other forms of volatile memories known in the art. In some examples, memory 83 is used to store program instructions for execution by processors 82. Memory 83, in one example, is used by software or applications running on server 106 to temporarily store information during program execution. Although memory 83 of FIG. 6 is not described as including field input data 92 or gesture actions 96, for example, memory 83 may store such instructions and other data in other examples.

Repository 108, in some examples, also includes one or more computer-readable storage media, such as one or more storage devices. Repository 108 may be configured to store larger amounts of information than memory 83. Repository 108 may further be configured for long-term storage of information. In some examples, repository 108 may include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Repository 108 may be configured to store information related to or collected from each of multiple patients. For example, repository 108 may be configured to store field input data 92 collected from one or more patients. The field input data 92 may include the raw data, or processed data, obtained from sensors 30 or other sensors configured to detect gesture input. Repository 108 may also include gesture input types 94, gesture actions 96, user specific information 98, gesture control schemes 100, and medical procedures 102. The data stored in repository 108 may also be stored in memory 62 of gesture control device 22 of FIG. 3, for example.

Gesture input types 94 may define the different types of gesture input that may be identified or determined by server 106. For example, gesture input types may include one or more indicator gesture input types, one or more control gesture input types, one or more confirmation gesture input types, and one or more termination gesture input types. A gesture input type may define a gesture that is used for a specific purpose. For example, a gesture type may be a hand with five outstretched fingers, a clenched fist, or the pinching motion of a pointer finger moving towards the thumb. Other example gesture types may include directional swipes (e.g., up, down, left, or right), hand or finger rotations (e.g., clockwise for an increase in a parameter such as amplitude or counter-clockwise for a decrease in a parameter such as amplitude), and changing between close and far away from the sensor to control an adjustment to a parameter. Relative movement gestures may be more easily detected by an IMD than more stationary gestures distinguishable by external sensors such as optical sensors. Each of these gesture input types 94 may be used by a user to request a specific input related to the gesture input type. In other words, gesture input types 94 may include a library of the different gestures detectable by server 106.

Gesture actions 96 may include a database of actions, or controls, that correspond to respective gesture input types. For example, gesture actions 96 may include such actions as insertion of a lead into patient 12 by a surgical device, turning ablation energy on and off, or increasing and decreasing the parameter value of electrical stimulation voltage. Gesture actions 96 may include each of the actions, or controls, and a link to the corresponding gesture input type that can be used to define or request each of the actions.

User specific gesture information 98 may include any information used to identify a particular user (e.g., a specific clinician) from the field input data 92 or determined gesture input. Thus, user specific gesture information 98 may include calibrated parameters or factors from which server 106 can determine whether or not a particular gesture input was provided by the specific user. In one example, a user may provide gestures having certain sizes, speeds, angles, or positions within an envelope. User specific gesture information 98 may quantify these specific features of each gesture provided by the user such that the gesture input is similar to a "fingerprint" of the user for the gesture input. Instead of merely determining that an outstretched hand and fingers or movement of a hand from one lower position to a higher position are a certain gesture input type, server 106 may be configured to determine what user provided those gesture inputs based on the user specific gesture information stored in repository 108. For example, different users may have respective different permissions or levels of allowable control using gesture inputs. In this manner, server 106 (or another device) may determine that a correct gesture was performed, but identify the gesture as provided by the wrong user (e.g., the wrong user being a user not identified as having permission to provide the detected gesture or a user different from the user that entered the gesture control mode). A user may need to perform a calibration session, or have previous gesture input analyzed, so that server 106 or another computing device can generate the user specific gesture information 98 for that particular user.

Gesture control schemes 100 may be a list of possible control schemes using gestures and algorithms needed to perform each scheme. A gesture control scheme may define how server 106 will control a medical device or another action for a medical procedure based on received gestures. For example, a gesture control scheme may require that an indicator gesture input must be received and a gesture control mode entered before server 106 can receive control gesture input and perform an action. Another gesture control scheme may include requiring a control gesture input and a confirmation gesture input to be received simultaneously in order for server 106 to control a device to perform an action. Each step of a medical procedure or process that can receive gesture input may link to one or more gesture control schemes 100 to identify how gesture input can be used for control of one or more devices.

Medical procedures 102 may include those medical procedures in which gesture input can be used to control one or more actions. Each of the medical procedures 102 may define one or more steps of the procedure and identify which step can accept gesture input to perform an action. In addition, each of medical procedures 102 may identify which gesture control schemes 100 can be used for control, such as whether or not a gesture control mode can be entered upon the start of a step or whether the gesture control mode should be exited in response to a step being completed. Gesture detection module 88 may incorporate one or more of the rules stored in repository 108 in determining the gesture input and how to control any actions based on the received gesture input. The rules and schemes described herein may be implemented to minimize any error related to gesture input control of actions related to medical procedures.

Server 106, in some examples, also includes a network interface 84. Server 106, in one example, utilizes network interface 84 to communicate with other computing devices (e.g., gesture control device 22 of FIG. 1), programmers (e.g., programmer 50 of FIG. 2), medical devices, or more networks, such as network 110 shown in FIG. 7. In this manner, server 106 may receive field input data 92 and transmit information such as gesture control information 114 (shown in FIG. 7). Network interface 84 may be a network interface card, such as an Ethernet card or other wired interface. In other examples, network interface 84 may include an optical transceiver, a radio frequency transceiver, or any other type of device that can send and receive information. Other examples of such network interfaces may include Bluetooth, 3G, 4G and WiFi radios in mobile computing devices as well as USB. In some examples, server 106 utilizes network interface 84 to wirelessly communicate with another computing device (e.g., gesture control device 22 of FIG. 1) or other networked computing devices.

Server 106, in one example, also includes one or more user interfaces 86. User interface 86 may include a touch-sensitive screen, mouse, a keyboard, a voice responsive system, camera, or any other type of device for detecting a command from a user. In one example, user interface 86 may include a touch-sensitive screen, sound card, a video graphics adapter card, or any other type of device for converting a signal into an appropriate form understandable to humans or machines. In addition, user interface 86 may include a speaker, a cathode ray tube (CRT) monitor, a liquid crystal display (LCD), or any other type of device that can generate intelligible output to a user.

Server 106, in some examples, includes one or more power sources 90, which provide power to server 106. Generally, power source 90 may utilize power obtained from a wall receptacle or other alternating current source. However, in other examples, power source 90, may include one or more rechargeable or non-rechargeable batteries (e.g., constructed from nickel-cadmium, lithium-ion, or other suitable material). In other examples, power source 90 may be a power source capable of providing stored power or voltage from another power source.

In other examples, one or more of processors 82 may perform some or all of the functions described herein within respect to gesture detection module 88. Any software implemented within or executed by server 106 may be implemented or contained within, operable by, executed by, and/or be operatively/communicatively coupled to components of server 106 (e.g., processors 82, memory 83, network interface 84, and/or repository 108).

FIG. 7 is a conceptual diagram illustrating example system 104 that includes networked server 106 of FIG. 6 for determining gesture input based on received field input data 64. As shown in FIG. 7, system 104 includes gesture control device 22, sensors 30, network 110, networked server 106 (e.g., a computing device), repository 108, and external programmer 50, and medical device 112. Gesture control device 22, in some examples, is or is a part of a computing device (e.g., a workstation, a netbook computer, a notebook computer, a tablet computing device, or server computing device). In any examples, gesture control device 22 may be a computing device configured to assist in the obtaining of gesture input and/or control of an action based on the gesture input. Gesture control device 22 may also include a display device (e.g., output device 24 of FIG. 3) and be configured to control the display device. The display device be housed by gesture control device 22 or be external to gesture control device 22. Although sensors 30 may be separate devices in communication with gesture control device 22, sensors 30 may be coupled to or at least partially within a housing of gesture control device 22 in other examples. In some examples, gesture control device 22 may receive field input data 64 from sensors 30, detect gesture input from the field input data 64, determine actions for a medical device (e.g., medical device 112) corresponding to the gesture input, and transmit control signals to the medical device based on the determined actions. However, as described in FIG. 7, one or more aspects of this gesture control process may be performed by a networked server (e.g., server 106) to take advantage of increased processing capabilities and/or centralize the gesture input process.

For example, gesture control device 22 may receive field input data 64 from one or more sensors 30. As described herein, sensors 30 may detect gestures from user 14 that are intended as gesture input (e.g., indicator, control, termination, or confirmation gesture input). Gesture control device 22 may be configured to connect to network 110 (e.g., a wired or wireless network). In some examples, gesture control device 22 may also be configured to communicate with networked server 106 via network 110 to transmit field input data 64. Although network 110 may be a single network, network 110 may be representative of two or more networks configured to provide network access to server 106 and/or repository 108. In general, gesture control device 22 may manage the collection and/or generation of field input data 64 and request server 106 to process field input data 64. However, in other examples, server 106 may provide greater control over gesture control device 22, such as requesting that gesture control device 22 begin obtaining field input data 64 from sensors 30.

Once received by gesture control device 22 via network 110, networked server 106 may be configured to store field input data 64 in repository 108 until the field input data is to be analyzed and/or for long-term storage. Both gesture control device 22 and networked server 106 may connect to network 110. Network 110 may be embodied as one or more of the Internet, a wireless network, a wired network, a cellular network, or a fiber optic network. In other words, network 110 may be any data communication protocol or protocols that facilitate data transfer between two or more devices. Networked server 106 may also connect to repository 108 to store and/or retrieve field input data 64 received from gesture control device 22, gesture input types, gesture actions, gesture control schemes, or any other data stored in repository 108.

Networked server 106 and repository 108 may each include one or more servers or databases, respectively. In this manner, networked server 106 and repository 108 may be embodied as any hardware necessary to process and/or store field input data 64 and any other information related to gesture input processing and control. Networked server 106 may include one or more servers, desktop computers, mainframes, minicomputers, or other computing devices capable of executing computer instructions and storing data. In some examples, functions attributable to networked server 106 herein may be attributed to respective different servers for respective functions. Repository 108 may include one or more memories, repositories, hard disks, or any other data storage device. In some examples, repository 108 may be included within networked server 106.

Repository 108 may be included in, or described as, cloud storage. In other words, field input data 64 or any other such information may be stored in one or more locations in the cloud (e.g., one or more repositories 108). Networked server 106 may access the cloud and retrieve the appropriate data as necessary. In some examples, repository 108 may include Relational Database Management System (RDBMS) software. In one example, repository 108 may be a relational database and accessed using a Structured Query Language (SQL) interface that is well known in the art. Repository 108 may alternatively be stored on a separate networked computing device and accessed by networked server 106 through a network interface or system bus. Repository 108 may thus be an RDBMS, an Object Database Management System (ODBMS), Online Analytical Processing (OLAP) database, or any other suitable data management system.

Once server 106 receives field input data 64, server 106 may process the field input data 64 to determine one or more gesture inputs from the field input data and/or determine the corresponding control requested by the gesture input. Server 106 may utilize any information or rules stored in repository 108 and/or received from gesture control device 22 along with field input data 64. For example, server 106 may generate gesture control information 114 that specifies the action to be completed by medical device 112 (e.g., IMD 18, a surgical device, an implantation device, or any other device configured to perform one or more actions on patient 12 during, or as a result of, a medical procedure). Gesture control information 114 may be generated according to the techniques described herein to mitigate error that may occur with gesture input. Gesture control information 114 may include an adjustment to a parameter value or some other command that at least partially controls an action of medical device 112.

Server 106 may transmit gesture control information 114 to another device via network 110. For example, server 106 may transmit gesture control information 114 to gesture control device 22 via network 110. In response to receiving the gesture control information 114, gesture control device 22 may transmit a control signal to medical device that commands medical device 112 to perform an action for a medical procedure related to patient 12. The control signal may be the same gesture control information 114 or a signal derived from gesture control information 114 and configured specifically for medical device 112. In other examples, server 106 may transmit gesture control information 114 to another device instead of gesture control device 22. Server 106 may transmit gesture control information 114 to external programmer 50 (e.g., a device that programs medical device 112) via network 110, and external programmer may respond by controlling medical device 112 according to gesture control information 114. In some examples, server 106 may transmit gesture control information 114 directly to medical device 112 via network 110 when medical device 112 is connected to network 110.

As described in FIG. 7, gesture input control of one or more medical devices may be performed by a distributed system over a network. In this manner, gesture control device 22 may function together with server 106 to control medical device 112 for a medical procedure. Server 106 may be located remote from gesture control device 22 and/or user 14 (e.g., in another building or even another city). Alternatively, server 106 may be located within the same room as user 14 and still utilize network 110 for transferring data. In some examples, multiple servers 106 may be accessible by gesture control device 22 such that if one of the servers is not available for any reason, another server may be used to process field input data 64. In other words, gesture control device 22 may select any available server 106 or a set of servers may operate together to provide redundancy for generating gesture control information 114.

Figure 8A:
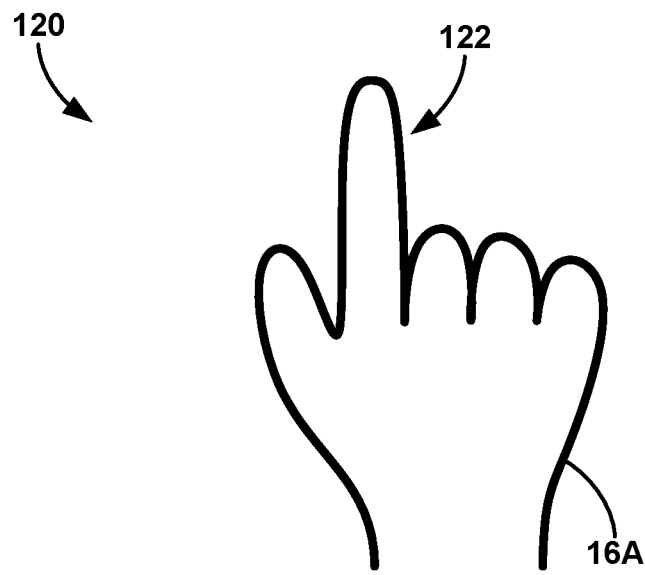
FIGS. 8A and 8B are conceptual diagrams of example gestures for an indication gesture input and a control gesture input.
Figure 8B:
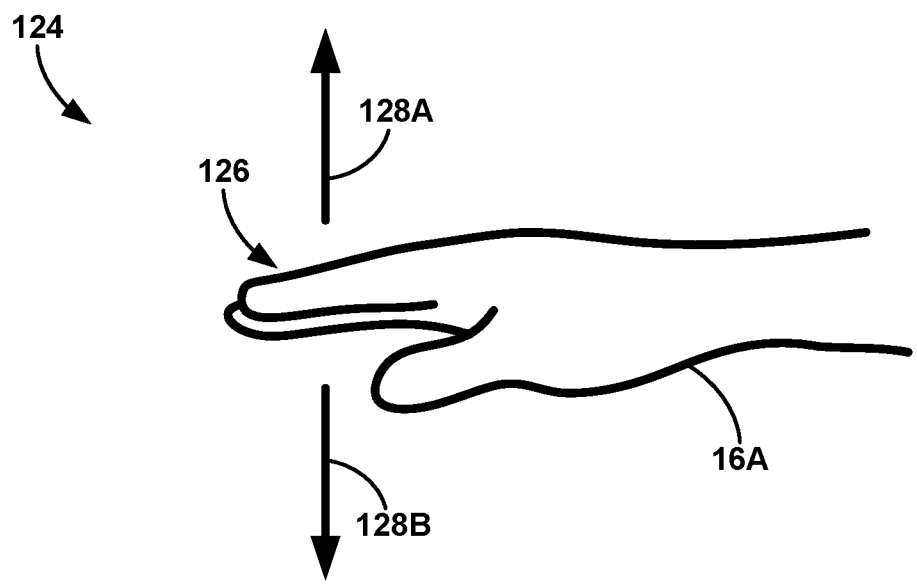

FIGS. 8A and 8B are conceptual diagrams of example gestures for an indication gesture input and a control gesture input. As shown in FIG. 8A, indication gesture input 120 includes a stationary index finger 122 extended from hand 16A with the remaining fingers and thumb rolled into a fist. Indication gesture input 120 may be used to signal the beginning of a gesture control mode such that gesture control device 22 can, for example, enable the gesture control mode in response to detecting indication gesture input 120.

Indication gesture inputs, such as indication gesture input 120, may result from any different types of gestures. For example, an indication gesture input may be a stationary configuration of one or two hands and/or a movement of one or two hands. In some examples, an indication gesture input may include a stationary configuration of a hand (e.g., hand 16A) to another hand (e.g., hand 16B) or anatomical structure such as a chin, forehead, ear, or shoulder of user 14. Any of these or other gestures may be used and identified by gesture control device 22 as an indication control gesture per the stored instructions.

As shown in FIG. 8B, example control gesture input 124 includes hand 16A with extended fingers 126 extended and positioned together. Control gesture input 124 also includes movement of hand 16 in the direction of one of arrows 128A or 128B. For example, movement of hand 16A in the "up" direction of arrow 128A may indicate an increase to a parameter value for the medical device. Alternatively, movement of hand 16A in the "down" direction of arrow 128B may indication a decrease to the parameter value for the medical device. In some examples, the direction of hand 16A towards the direction of either arrow 128A or 128B may be identified as separate gesture inputs.

A control gesture input, such as control gesture input 124, may include movement of a hand between two locations in space. In other examples, a control gesture input may include repetitive hand motions (e.g., circular movements, rotational movement such as representing the turning of a knob, up and down movements, or side to side movements). Other control gesture inputs may include movement of two or more fingers with respect to other fingers, movement of two hands with respect to each other, sequential stationary hand configurations, extending a specific number of fingers.

Control gesture inputs may be different from indicator gesture input. For example, control gesture inputs may include some change of one or more hands in space or configuration to indicate the desired change in a parameter value. An indicator gesture input may include a more stationary hand configuration that, when detected, causes gesture control device 22 to enter the gesture control mode. Gesture control device 22 may present feedback to user 14 regarding the gesture, such as the motion that was detected, the hand configuration detected, a representation of the actual gesture input detected, and/or the resulting change in parameter value identified based on the received gesture input. Indication gesture input may be received sequentially to gesture control input. In other words, gesture control device 22 may need to detect the indication gesture input first such that the gesture control mode can be entered, and gesture control device 22 can then detect the control gesture input. Alternatively, indicator gesture input may be received simultaneously to the control gesture input (e.g., one hand provides the indicator gesture input while the other hand provides the control gesture input).

Figure 9A:
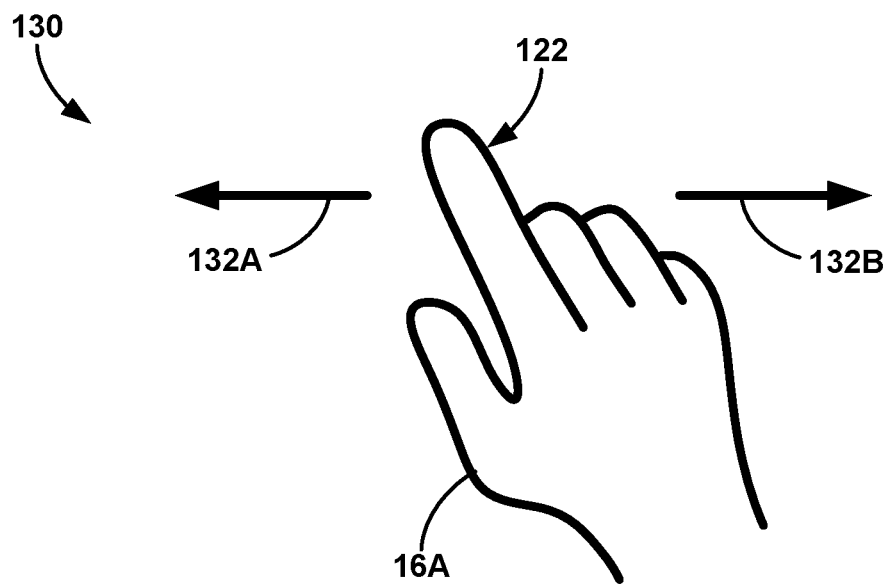
FIGS. 9A and 9B are conceptual diagrams of example gestures for a control gesture input and a confirmation gesture input.
Figure 9B:
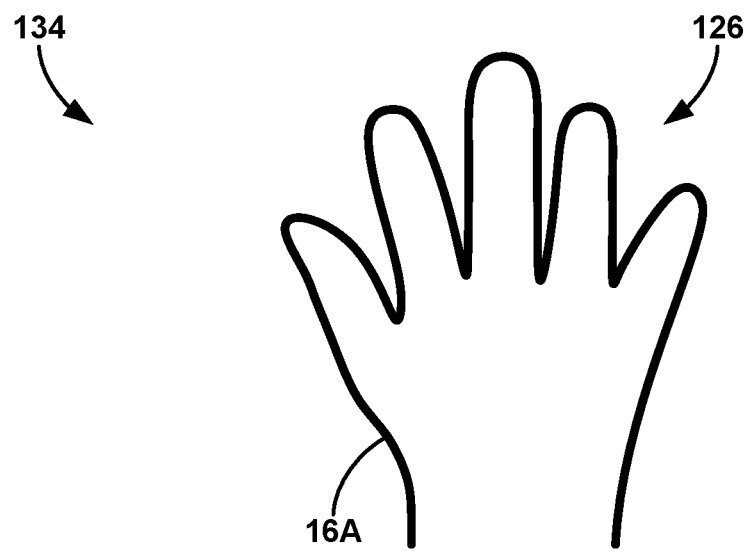

FIGS. 9A and 9B are conceptual diagrams of example gestures for control gesture input 130 and confirmation gesture input 134. As shown in FIG. 9A, control gesture input 130 may include hand 16A with an extended index finger 122 with movement of hand 16A in the direction of arrow 132A or 132B. In this manner, control gesture input 130 may provide a movement that indicates whether to increase or decrease a parameter value. In other examples, two or more of the fingers of hand 16A may be extended during gesture control input 130. The number of fingers, or a specific one or more fingers of hand 16A, may be extended during control gesture input 130 to specify a respective parameter to be controlled by the gesture input. Control gesture input 130 may be similar to control gesture inputs described in FIG. 8B. In some examples, a control gesture may require two hands instead of one.

Confirmation gesture input 134 may provide a relatively low error gesture, i.e., a gesture that has a low likelihood of being erroneously interpreted or recognized, to confirm that control gesture input 130 was requested. A low error gesture may include a hand configuration or hand motion that is easily identifiable and distinguishable from other types of gestures. A low error gesture may also be a gesture that user 14 would not typically make during ordinary actions of the user so that the confirmation gesture input is not made inadvertently. For example, example confirmation gesture input 134 may include hand 16A with all fingers and thumb extended out and separated. Gesture control device 22 may identify this configuration as the confirmation gesture input.

Confirmation gesture input 134 may be different from any of the gestures that may be used as a control gesture input. As discussed above, gesture control device 22 may provide feedback to the user regarding what gesture was detected. Control gesture input and confirmation gesture input may be received sequentially such that the confirmation gesture input is provided immediately after the control gesture input and without any intervening gesture. Alternatively, control gesture input and confirmation gesture input may be provided simultaneously (e.g., hand 16A may provide control gesture input 130 and hand 15B may provide confirmation gesture input 134).

Figure 10:
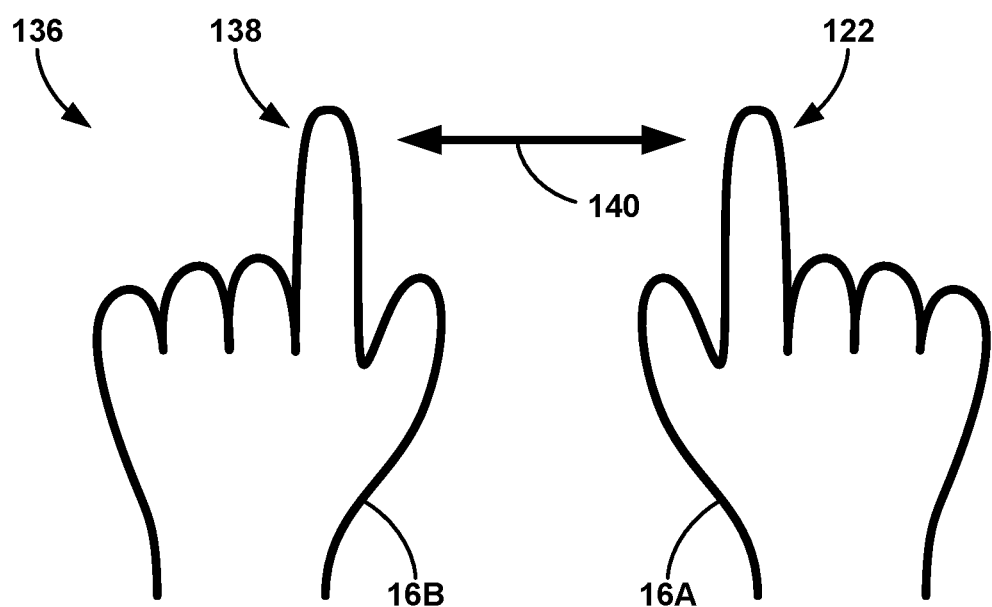
FIG. 10 is a conceptual diagram of example gesture that is authenticated as provided by a particular user.

FIG. 10 is a conceptual diagram of example gesture that is authenticated as provided by a particular user. Control gesture input 136 may be a control gesture input that is authenticated to a particular user before gesture control device 22 controls an action based on the received control gesture input. Control gesture input 136 may include hand 16A with extended index finger 122 and hand 16B with index finger 138 extended, and user 14 moves hands 16A and 16B closer or farther away, relative to one another, in the direction of arrow 140 to indicate the desired change in control. For example, increasing the distance between fingers 122 and 138 may indicate an increase in the parameter value and decreasing the distance may indicate a decrease in the parameter value.

Gesture control device 22 may analyze the gesture for one or more aspects specific to the user 14. For example, gesture control device 22 may measure a length of one or both of fingers 122 and 138, determine a difference in length between fingers 122 and 138, a rate of movement of hands 16A and 16B, a positioning of a thumb, or any other aspects of hands 16A and 16B or control gesture input 136 that may be specific to a user. Gesture control device 22 may require two or more aspects for authentication in some examples. Gesture control device 22 may store calibration data from previous gesture inputs of user 14 to determine the gesture "fingerprint" specific to user 14. Authentication of control gesture input 136 may prevent unauthorized or inadvertent gesture inputs provided by someone other than the intended user 14.

FIGS. 11-17 are flow diagrams illustrating various processes and techniques that may be used to detect and determine gesture input for controlling one or more actions of a medical procedure. Typically, the control is of one or more medical devices that perform the action. Generally, one or more processors 60 of gesture control device 22 and/or processors 82 of networked server 106 are described as performing the described processes in FIGS. 11-17. However, the processes may be performed by one or more other devices or systems (e.g., external programmer 50 or combinations of different processors and/or devices in other examples.) For example purposes, gesture control device 22 and processor 60 of system 10 will be described in the example techniques of FIGS. 11-17. In other examples, a gesture detection module similar to gesture detection module 88 of server 106 may perform these functions of gesture control device 22.

Figure 11:
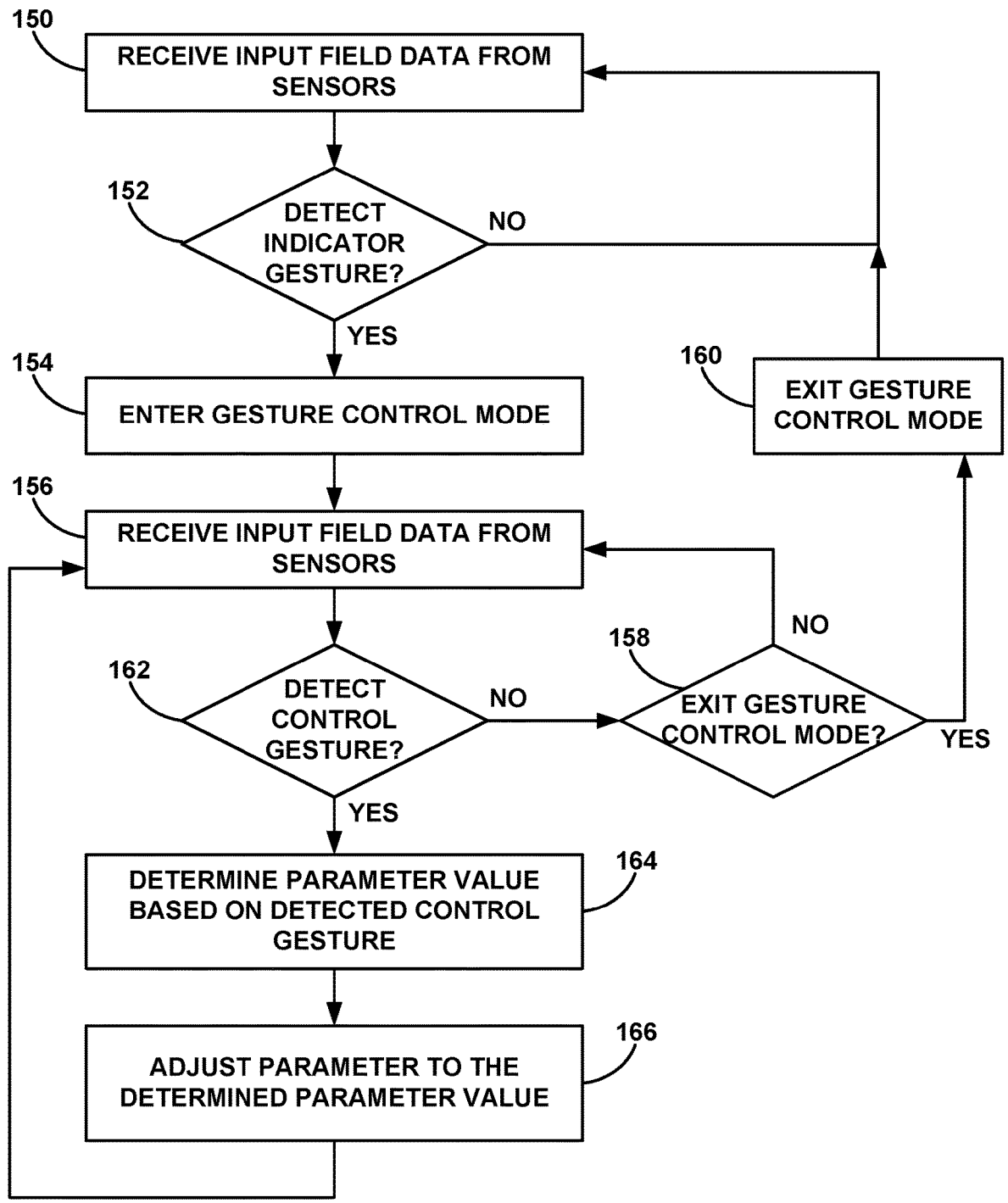
FIG. 11 is a flow diagram that illustrates an example process for entering a gesture control mode in response to receiving an indicator gesture input.

FIG. 11 is a flow diagram that illustrates an example process for entering a gesture control mode in response to receiving an indicator gesture input. As shown in FIG. 11, processor 60 of gesture control device 22 receives input field data from sensors 30 (150) and detects whether or not an indicator gesture input was received from user 14 (152). If processor 60 does not detect an indicator gesture input ("NO" branch of block 152), processor 60 continues to receive additional field input data (150). If processor 60 does detect an indicator gesture input ("YES" branch of block 152), processor 60 enters the gesture control mode that can accept control gesture input (154).

Processor 60 then receives additional input field data from sensors 30 (156). If processor 60 does not detect a control gesture input ("NO" branch of block 162), processor 60 checks to determine if the gesture control mode should be exited (158) (e.g., a termination gesture input has been received). If processor 60 determines that the gesture control mode should not be exited ("NO" branch of block 158), processor 60 may continue to receive additional field input data (156). If processor 60 determines that the gesture control mode should be exited ("YES" branch of block 158), processor 60 exits the gesture control mode (160) and continues to receive input field data (150).

If processor 60 does detect a control gesture input ("YES" branch of block 162), processor 60 determines the parameter value based on the detected control gesture input (164). For example, processor 60 may search a database for parameter value that corresponds to the received control gesture input or otherwise apply the control gesture input to one or more rules to generate the new parameter value. Processor 60 then controls a medical device to adjust the parameter to the new determined parameter value (166). In this manner, processor 60 can control an action for a medical procedure by controlling a medical device to perform the specified action requested by the gesture input. Processor 60 then continues to receive input field data during the gesture control mode (156) until the gesture control mode is exited.

Figure 12:
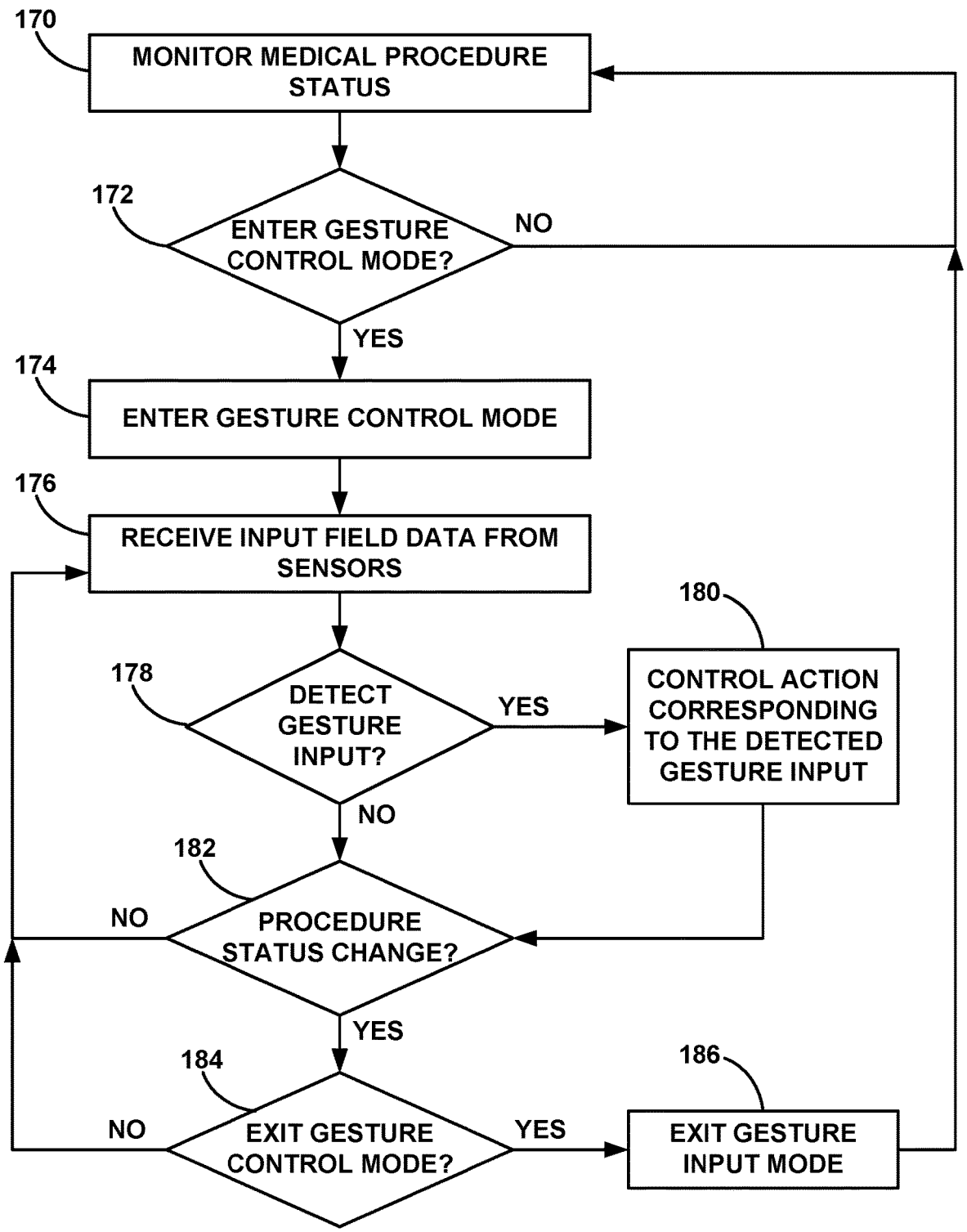
FIG. 12 is a flow diagram that illustrates an example process for exiting a gesture control mode in response to a change in a medical procedure.

FIG. 12 is a flow diagram that illustrates an example process for exiting a gesture control mode in response to a change in a medical procedure. As shown in FIG. 12, processor 60 of gesture control device 22 monitors the status of a medical procedure such as which step is currently engaged by user 14 (170). Processor 60 analyzes the medical procedure and detect when a step of the medical procedure has been started in which gesture control is allowed or required. If processor 60 does not determine that the current step is associated with a gesture control mode ("NO" branch of block 172), processor 60 continues to monitor the medical procedure for changes (170). If processor 60 does determine that the step of the medical procedure is associated with a gesture control mode, ("YES" branch of block 172), processor 60 enters the gesture control mode that can accept control gesture input (174).

Processor 60 then receives input field data from sensors 30 (176). If processor 60 does detect a control gesture input ("YES" branch of block 178), processor 60 determines the parameter value based on the detected control gesture input and controls an action of a medical device that corresponds to the detected gesture input (180). For example, processor

60 may control a medical device to adjust the parameter to a newly determined parameter value, based on the gesture input, during the current step of the medical procedure. Although the step of the medical procedure may remain the same after completion of the action, completing the action based on the control gesture input may trigger termination of the gesture control mode. Processor 60 then determines whether the status (or step) of the medical procedure has changed (182).

If processor 60 does not detect a control gesture input ("NO" branch of block 178), processor 60 checks to determine if the medical procedure status has changed (e.g., a new step has been entered or current step exited) (182). If processor 60 determines that the status of the medical procedure has not changed ("NO" branch of block 182), the processor continues to receive input field data (176). If processor 60 determines that the medical procedure status has changed ("YES" branch of block 182), processor 60 determines whether or not to exit the gesture control mode (184) (e.g., a new step is not associated with the gesture control mode). If processor 60 determines that the gesture control mode should not be exited ("NO" branch of block 184), processor 60 may continue to receive additional field input data (176). If processor 60 determines that the gesture control mode should be exited ("YES" branch of block 184), processor 60 exits the gesture control mode (186) and continues to receive input field data (170).

Figure 13:
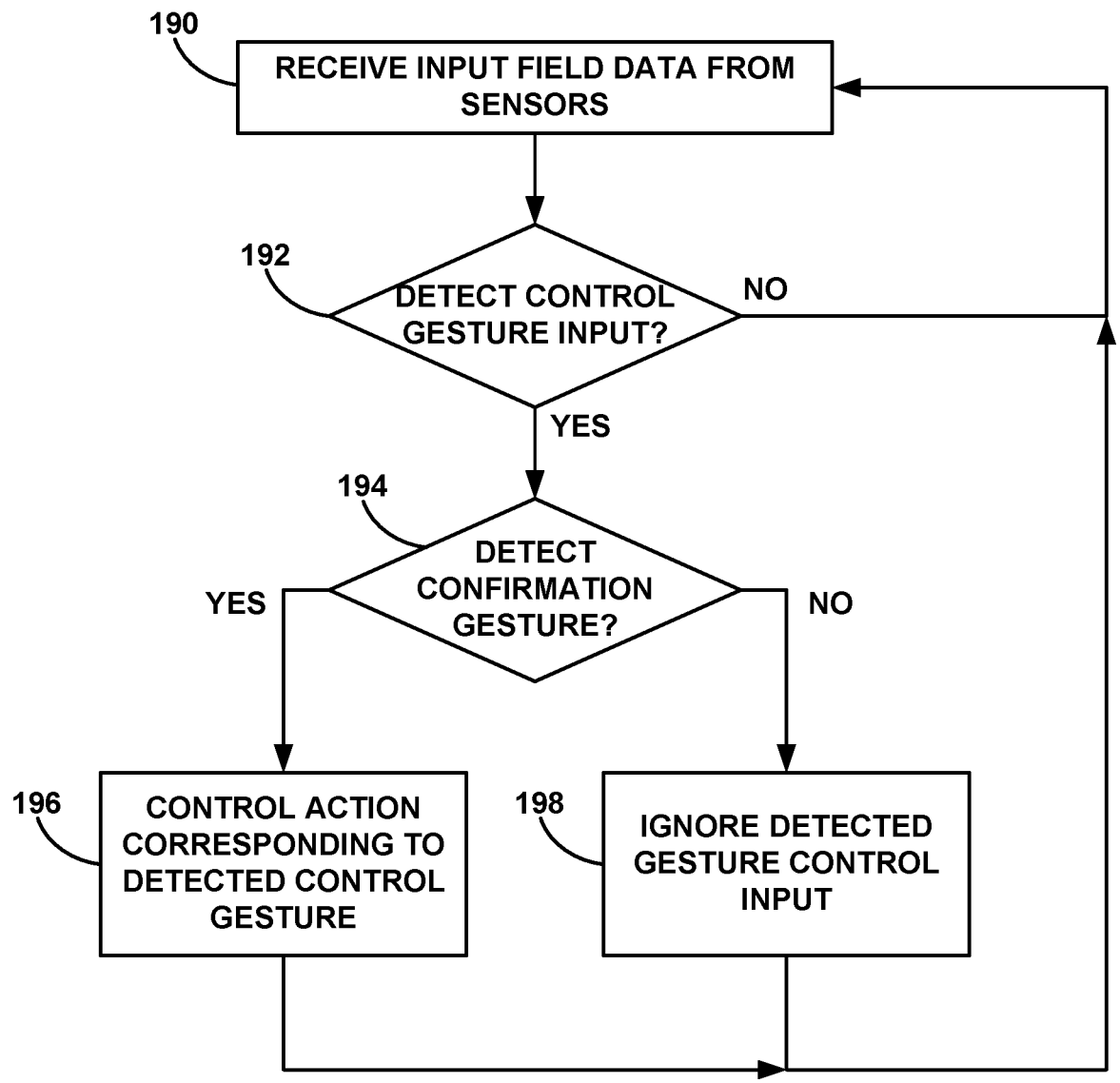
FIG. 13 is a flow diagram that illustrates an example process for receiving a confirmation gesture input that confirms a control gesture input.

FIG. 13 is a flow diagram that illustrates an example process for receiving a confirmation gesture input that confirms a control gesture input. As shown in FIG. 13, processor 60 of gesture control device 22 receives input field data from sensors 30 (190) and detects whether or not a control gesture input was received from user 14 (192). If processor 60 does not detect a control gesture input ("NO" branch of block 192), processor 60 continues to receive additional field input data (190). If processor 60 does detect a control gesture input ("YES" branch of block 192), processor 60 determines whether or not a confirmation gesture input was received (194).

If processor 60 does not detect a confirmation gesture input ("NO" branch of block 194), processor 60 ignores the detected control gesture input (198). In other words, the confirmation control input is requested before processor 60 will control any medical device based on the control gesture input. In some examples, processor 60 may wait a predetermined period of time or for some subsequent event (e.g., another control gesture input) before determining that no confirmation gesture input was detected). If processor 60 determines that a confirmation gesture input was received ("YES" branch of block 194), processor 60 controls an action of a medical device for the medical procedure corresponding to the received control gesture input (196). For example, processor 60 may determine a new parameter value based on the detected control gesture input and transmit the new parameter value to the medical device for adjustment of the parameter. Processor 60 then continues to receive input field data (190).

In the example of FIG. 13, processor 60 determines whether the confirmation gesture input was received subsequent to the control gesture input. However, in other examples, processor 60 may be configured to detect receiving the control gesture input simultaneously with the confirmation gesture input. In some examples, processor 60 may even require that the control gesture input was detected simultaneously (e.g., at least partially overlapping in time) with the confirmation gesture input. The confirmation gesture input of FIG. 13 may be used in conjunction with other error mitigation techniques, such as the gesture control mode of FIGS. 11 and/or 12. In this manner, multiple error mitigation techniques may be used in conjunction with each other for additional prevention of inadvertent gesture inputs.

Figure 14:
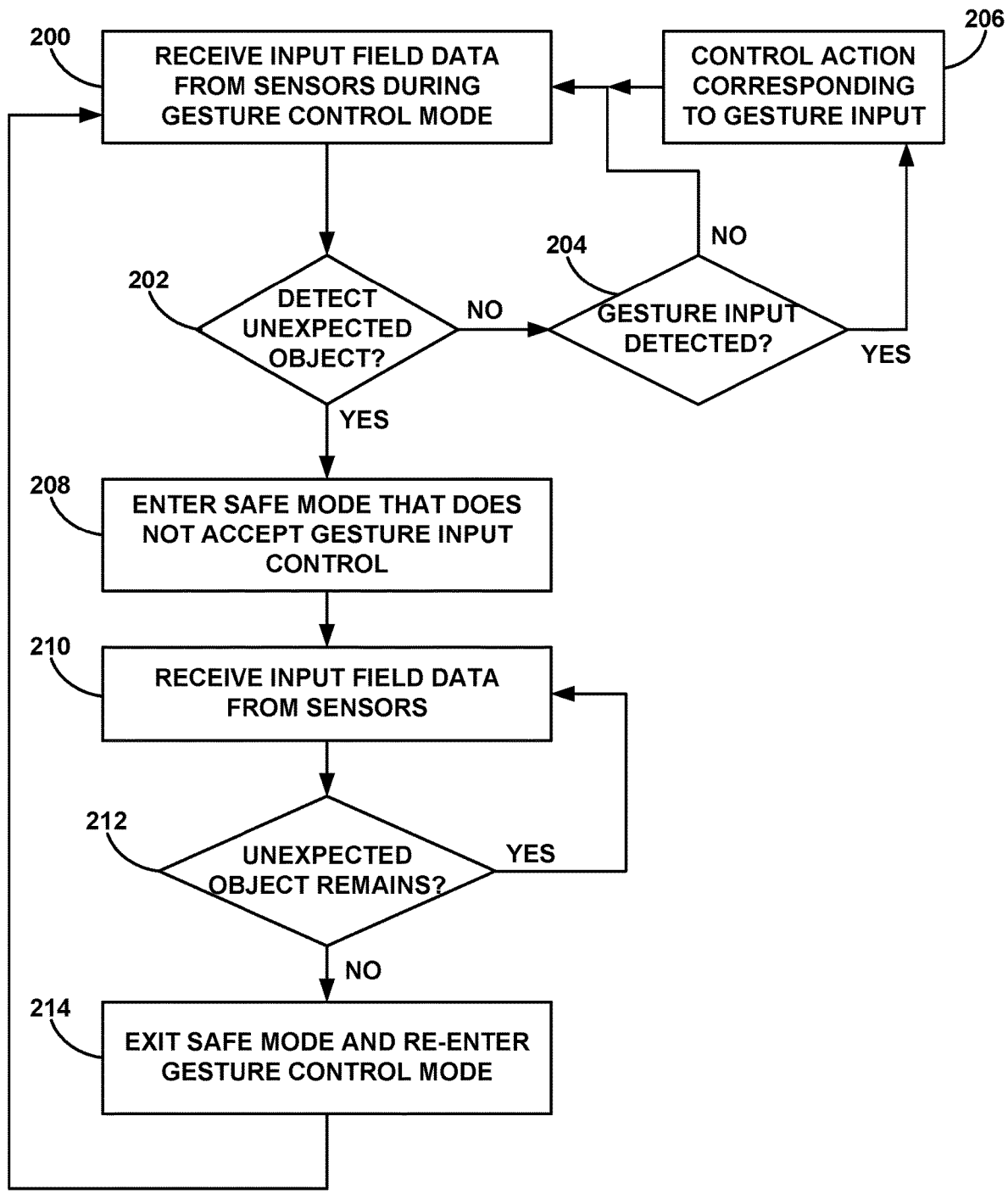
FIG. 14 is a flow diagram that illustrates an example process for suspending a gesture control mode in response to detecting an unexpected object within en envelope within which gesture input is detected.

FIG. 14 is a flow diagram that illustrates an example process for suspending a gesture control mode in response to detecting an unexpected object within en envelope within which gesture input is detected. As shown in FIG. 14, processor 60 receives input field data from sensors 30 during an active gesture control mode (200). If processor 60 has not detected an unexpected in the same envelope or area in which gestures are detected by sensors 30 ("NO" branch of block 202), processor 60 determines whether or not a control gesture input was detected (204). If processor 60 detects a control gesture input ("YES" branch of block 204), processor 60 controls a medical device to perform an action corresponding to the control gesture input (206) and continues to receive input field data (200). If processor 60 does not detect any control gesture input ("NO" branch of block 204), processor 60 continues to receive field input data from sensors 30 (200).

If processor 60 detects an unexpected object from the field input data ("YES" branch of block 202), the processor enters a safe mode that does not accept a control gesture input (208). In other words, processor 60 does not act on any received control gesture input during the safe mode. The safe mode may also be referred to the period of time during which the gesture control mode has been suspended or exited. During the safe mode, processor 60 continues to receive field input data from sensors 30 (210). If processor 60 determines that the unexpected object remains in the envelope ("YES" branch of block 212), processor 60 continues to receive and analyze the field input data (210). If processor 60 determines that the unexpected object no longer remains ("NO" branch of block 212), processor 60 exits the safe mode and re-enters (of unsuspends) the gesture control mode such that processor 60 can again control a medical device based on received control gesture input (214).

An unexpected object may be a third hand (indicating that another user is present and erroneous gestures may be detected) or an object that has been placed between one or more of sensors 30 and user 14. In any case, processor 60 may determine that the unexpected object, or anomaly, may reduce the accuracy of the field input data for gesture input detection. In some examples, processor 60 may end the safe mode in response to determining other events. For example, processor 60 may end the safe mode (i.e., re-enter the gesture control mode) in response to determining that an error with input field data no longer exists, the safe mode has reached a predetermined timeout, or determining that a non-gesture input over-riding the safe mode has been received.

Figure 15:
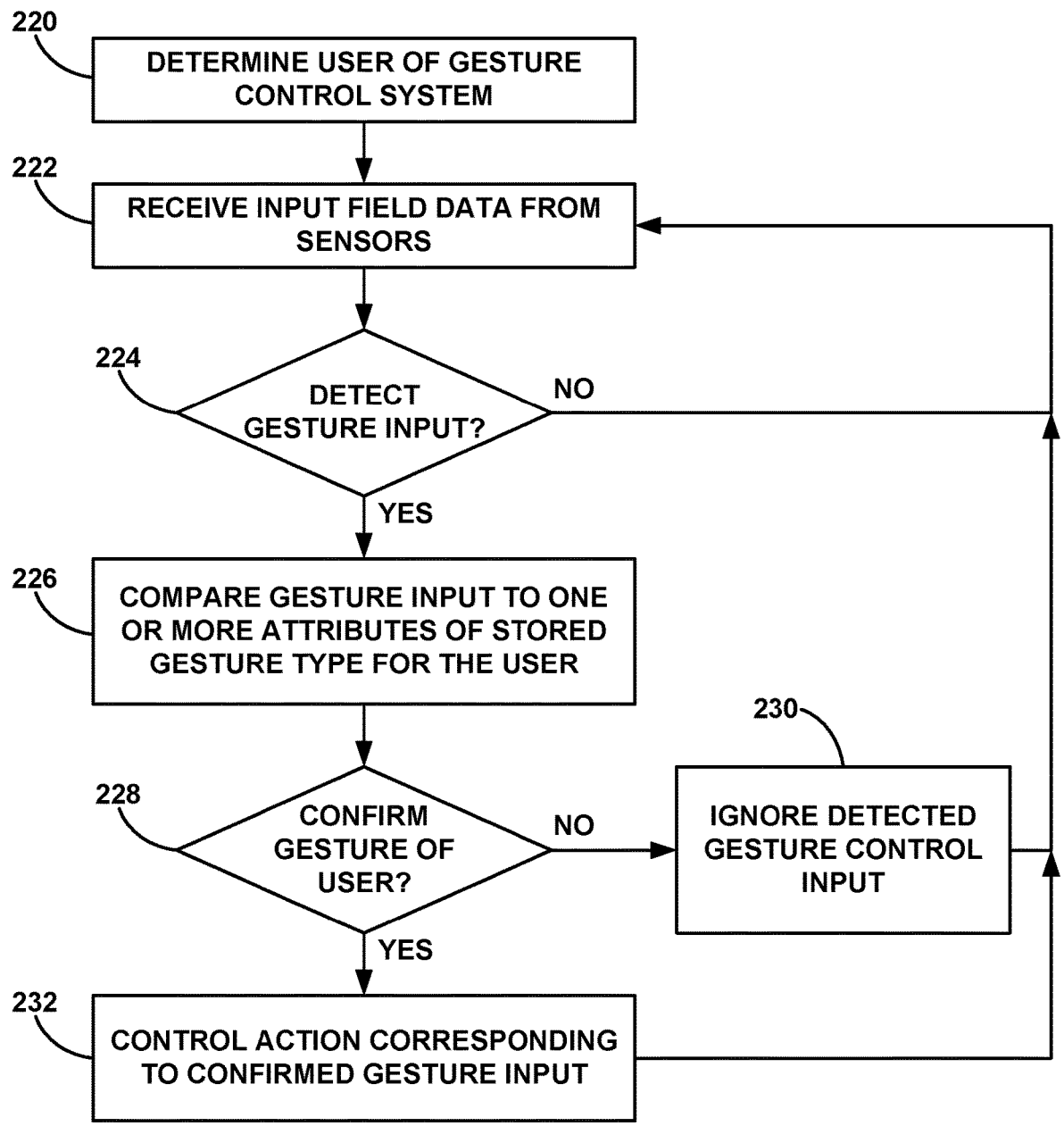
FIG. 15 is a flow diagram that illustrates an example process for confirming a gesture input is from an expected user.

FIG. 15 is a flow diagram that illustrates an example process for confirming a gesture input is from an expected user. As shown in FIG. 15, processor 60 determines the user of gesture control device 22 or the user that should otherwise be providing gesture input (220). This step may require receiving an input identifying the user (e.g., username and/or password or biometric parameter). Once the user of the system has been determined, processor 60 of gesture control device 22 receives input field data from sensors 30 (222). Processor 60 then detects whether or not a control gesture input was received (224). If processor 60 does not detect a control gesture input ("NO" branch of block 224), processor 60 continues to receive additional field input data (222).

If processor 60 does detect a control gesture input ("YES" branch of block 224), processor 60 compares the control gesture input to one or more attributes of a stored gesture type for the identified user (226). In other words, processor 60 may determine that one or more aspects of the received control gesture input correlates to respective attributes of the user. Aspects of the received control gesture input may include one or more dimensions of the hands and/or fingers in the control gesture, a rate of the motion of the gesture, a magnitude of the control gesture, a position within the envelope of sensors 30 for which the gesture was received, or any other aspect. The attributes of the user may be stored based on a calibration session in which the user previously performed the control gesture input or other measurements or motions regarding fingers, hands, or any other anatomical structure.

If processor 60 cannot confirm that the control gesture input correlates to the expected user ("NO" branch of block 228), processor 60 may ignore the detected control gesture input (230) and continue receiving field input data (222). In other examples, processor 60 may suspend or exit the gesture control mode in response to determining that the control gesture input does not correlate to the expected user. If processor 60 confirms that the control gesture input corresponds to the expected user ("YES" branch of block 228), processor 60 controls an action of a medical device for the medical procedure corresponding to the received control gesture input (232). Processor 60 then continues to receive input field data (222).

If the user determines that processor 60 is not correctly identifying the user, processor 60 may be configured to receive user input requesting recalibration of gesture input. Processor 60 may then confirm the identity of the user and perform a calibration application for the user in which attributes of the user can be derived from example gestures performed by the user. In response to completion of the calibration process, processor 60 may again enter the gesture control mode for the user and again receive input field data (222).

Figure 16:
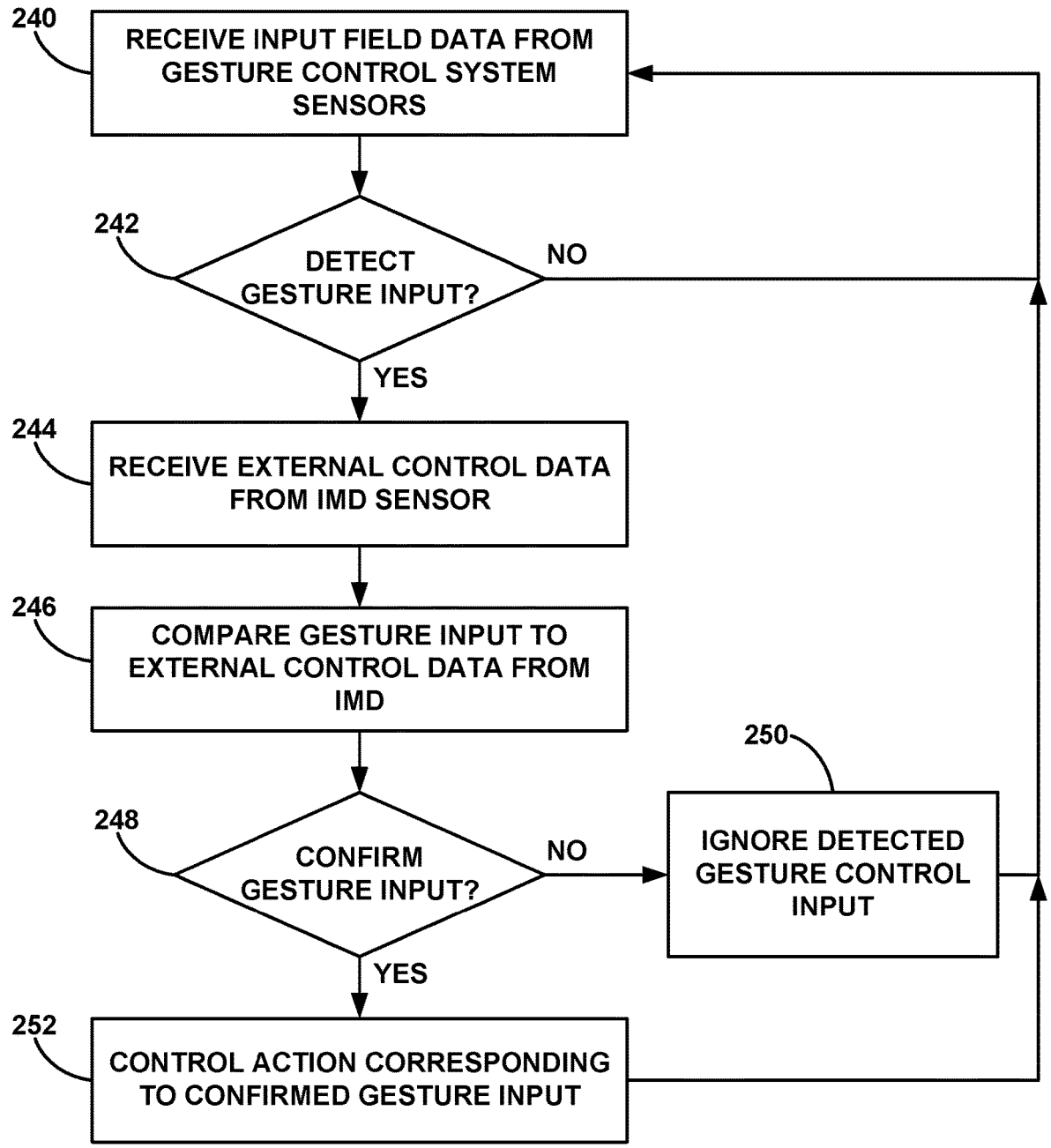
FIG. 16 is a flow diagram that illustrates an example process for detecting a gesture input based on data generated from an external sensor and an implantable medical device.

FIG. 16 is a flow diagram that illustrates an example process for detecting a gesture input based on data generated from an external sensor and an IMD. In this manner, the IMD may provide data that confirms the gesture input is accurate. As shown in FIG. 16, processor 60 of gesture control device 22 receives input field data from sensors 30 (240). Processor 60 then detects whether or not a control gesture input was received (242). If processor 60 does not detect a control gesture input ("NO" branch of block 242), processor 60 continues to receive additional input field data (240).

If processor 60 does detect a control gesture input ("YES" branch of block 242), processor 60 receives external control data from a sensor of IMD 18, for example (244). The IMD sensor may be one or more electrodes, one or more accelerometers, one or more ultrasound transducers, or any other sensors that may detect the presence of the hands of user 14. Processor 60 may then compare the control gesture input to the external control data from IMD 18. For example, processor 60 may determine that the control gesture input occurred within a same area in which IMD 18 detected the presence of the hands. Alternatively, IMD 18 may detect motion of the detected hands, instead of just indicating that the hands were detected, in order to provide additional information regarding the motion of detected hands with respect to IMD 18. Processor 60 may then correlate the gesture control input to the general motion detected by IMD 18. In any event, processor 60 may use the comparison of the gesture control input to the data from IMD 18 to confirm the accuracy of the control gesture input.

If processor 60 cannot confirm that the control gesture input correlates to the data from IMD 18 ("NO" branch of block 248), processor 60 may ignore the detected control gesture input (250) and continue receiving field input data (240). In other examples, processor 60 may suspend or exit the gesture control mode in response to determining that the control gesture input does not correlate to the expected user. If processor 60 confirms that the control gesture input is accurate ("YES" branch of block 248), processor 60 controls an action of a medical device for the medical procedure corresponding to the received control gesture input (252). Processor 60 then continues to receive input field data (240).

In other examples, processor 60 may receive the external control data contemporaneously (e.g., at the same time) as the field input data. In this manner, processor 60 may periodically or continuously receive both field input data from sensors 30 and external control data from IMD 18. Alternatively, processor 60 may only request external control data from IMD 18 in response to detecting control gesture input. Although external control data has been described for use in confirming control gesture input, processor 60 may confirm other gesture inputs, such as indicator gesture inputs, confirmation gesture inputs, or termination gesture inputs, in other examples.

Figure 17:
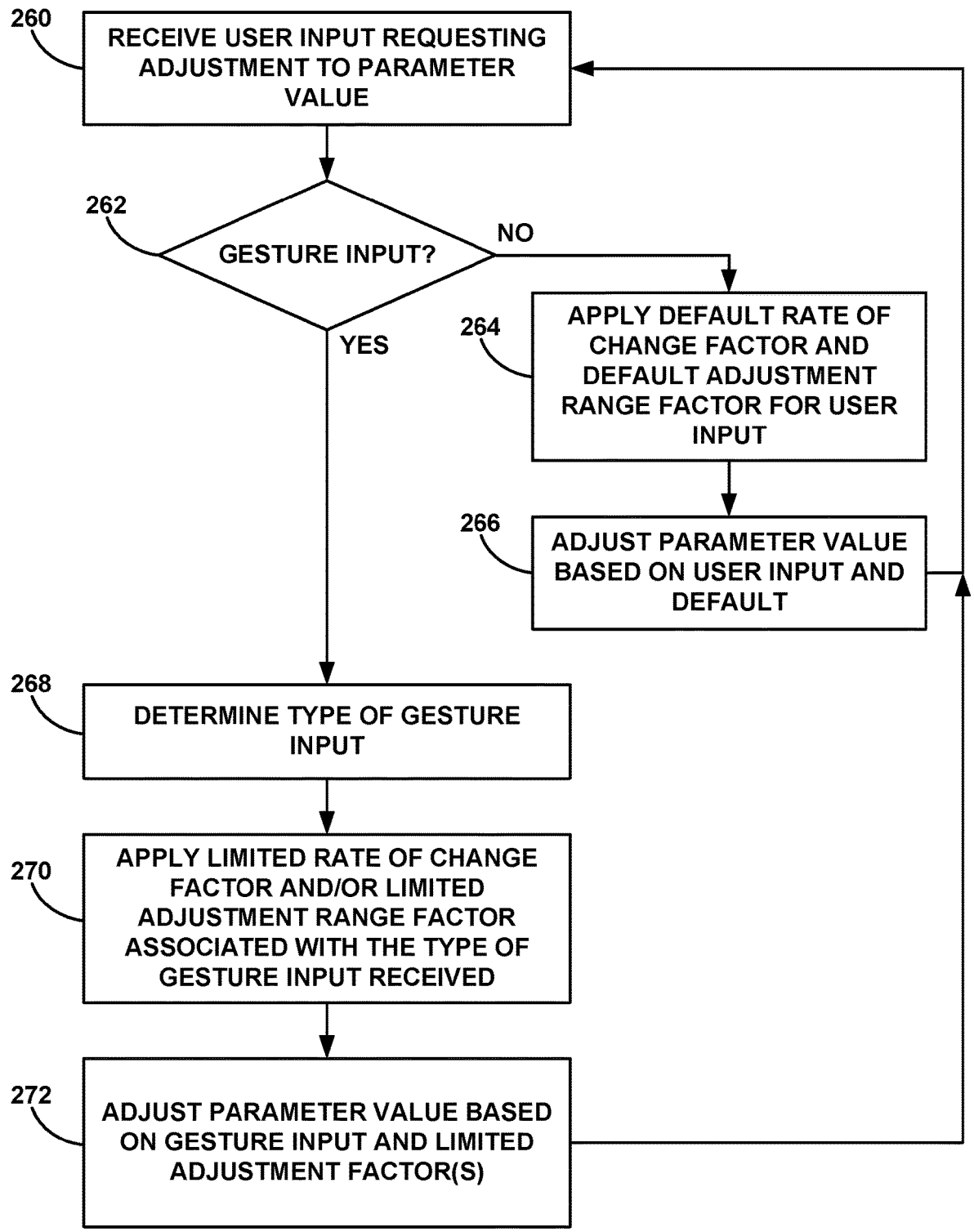
FIG. 17 is a flow diagram that illustrates an example process for limiting adjustments to parameters for gesture inputs.

FIG. 17 is a flow diagram that illustrates an example process for limiting adjustments to parameter values for gesture inputs. As shown in FIG. 17, processor 60 of gesture control device 22 receives user input requesting adjustment of a parameter value (260). Processor 60 then determines whether or not the user input was a gesture input or an input received via non-gesture input devices (262). If processor 60 determines that the user input is not a gesture input ("NO" branch of block 262), processor 60 applies a default rate of change factor and default adjustment range factor for the user input controlling the medical device (264). The default rate of change factor or default adjustment range factor may be a factor applied to signals from knobs, switches, or sliding devices. The rate of change factor indicates how much to adjust a parameter value for a corresponding movement of the input device. The default adjustment range factor indicates the amount of change that can occur to a parameter value from a single movement of the input device. Processor 60 may then adjust the parameter value based on the user input and the default factors (266) and again receive user input (260).

If processor 60 detects the user input is a gesture input ("YES" branch of block 262), processor 60 determines the type of gesture input (268). The type of gesture input may be the specific gesture that corresponds to a respective action of a medical device. For example, the type of gesture input may be a finger pinch or a hand elevation change. Processor 60 then applies a limited rate of change factor and/or a limited adjustment range factor associated with the type of gesture input received (270). The limited rate of change factor may limit how fast a parameter value can be changed due to hand motion (i.e., prevent large magnitude parameter value changes due to small hand movements). The limited adjustment range factor may limit the magnitude of parameter value adjustment from a single gesture input. These limited factors may prevent inadvertent or unintended parameter value changes due to gesture input. Processor 60 may then adjust the parameter value based on the gesture input and the one or more limited adjustment factors (272). Processor 60 may then again receive user input (260).

The limited rate of change factor and/or limited adjustment range factor may be specific to the type of gesture input. For example, the limited rate of change factor for a single hand movement gesture may be greater than the limited rate of change factor for a gesture of two hands moving with respect to each other (e.g., the single hand movement input is more limited to the adjustment that can occur). Each gesture type, or group of gesture types, may have respective limited factors. The limited factors may be based on calibration from user provided gestures and/or the user may directly adjust the limited factors. In some examples, the limited factors may be different for different steps of the medical procedure.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to gesture control device 22, external programmer 50, networked server 106, or medical devices 18 or 112, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between gesture control device 22 and networked server 106. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as one or more storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method comprising:
receiving, by processing circuitry, an indication to enter a gesture control mode during which the processor is configured to control one or more actions related to a medical procedure;
responsive to receiving the indication, entering, by the processing circuitry, the gesture control mode;
monitoring, by the processing circuitry, field input data received during the gesture control mode for one or more control gesture inputs, the one or more control gesture inputs requesting the processing circuitry control the one or more actions related to the medical procedure;
determining, by the processing circuitry and from the field input data, that an unexpected object is in an envelope within which the one or more control gesture inputs can be sensed, wherein the unexpected object is different than a user hand from which the one or more control gesture inputs are detectable; and
responsive to determining that the unexpected object is in the envelope, suspending, by the processing circuitry, the gesture control mode to prevent detection of erroneous gesture input due to the unexpected object.

2. The method of claim 1, further comprising:
determining to exit the gesture control mode; and
responsive to determining to exit the gesture control mode, exiting the gesture control mode, wherein exiting the gesture control mode disables gesture input control of the one or more actions related to the medical procedure.

3. The method of claim 2, wherein determining to exit the gesture control mode comprises:
monitoring progress of the medical procedure, wherein the medical procedure comprises a plurality of steps, one step of the plurality of steps being configured to accept the one or more control gesture input controlling the one or more actions related to the medical procedure during the one step;
determining that the one step of the medical procedure has been completed; and
responsive to determining that the one step has been completed, exiting the gesture control mode.

4. The method of claim 3, wherein the one step is a first step of the plurality of steps, and wherein the method further comprises:
- accepting the one or more control gesture inputs of a first plurality of gesture inputs during the first step;
- determining that the medical procedure has entered a second step of the plurality of steps of the medical procedure;
- responsive to the determination that the medical procedure has entered the second step of the plurality of steps of the medical procedure, entering the gesture control mode;
- accepting one or more gesture inputs of a second plurality of gesture inputs during the second step, the second plurality of gesture inputs being different than the first plurality of gesture inputs;
- determining that the second step of the medical procedure has been completed; and
- responsive to determining that the second step has been completed, exiting the gesture control mode for the second step.

5. The method of claim 2, wherein determining to exit the gesture control mode comprises:
- tracking a duration of time from when the gesture control mode was entered;
- comparing the duration of time to a predetermined gesture control timeout;
- determining that the duration of time exceeds the predetermined gesture control timeout; and
- responsive to determining that the duration of time exceeds the predetermined gesture control timeout, exiting the gesture control mode.

6. The method of claim 5, wherein the predetermined gesture control timeout is a first gesture control timeout specific to a first step of a plurality of steps of the medical procedure, the gesture control mode is entered during the first step, and the first gesture control timeout is different from a second gesture control timeout specific to a second step of the plurality of steps of the medical procedure.

7. The method of claim 1, wherein the field input data comprises first field input data received during the gesture control mode, and wherein the method further comprises:
- receiving second field input data during the suspension of the gesture control mode;
- detecting, from the second field input data, that the unexpected object is no longer in the envelope; and
- responsive to detecting that the unexpected object is no longer in the envelope, re-entering the gesture control mode.

8. The method of claim 1, wherein control of the one or more actions related to the medical procedure comprises adjustment of a parameter that at least partially defines a medical therapy.

9. The method of claim 1, wherein control of the one or more actions of the medical procedure comprises control of a surgical device to operate with respect to a patient receiving the medical procedure.

10. The method of claim 1, wherein the medical procedure comprises a surgical procedure.

11. The method of claim 1, wherein the medical procedure comprises an implantation of one or more medical devices.

12. The method of claim 1, wherein the medical procedure comprises adjusting one or more parameters that at least partially define electrical stimulation therapy.

13. The method of claim 1, wherein the processor is housed within one of a networked server, a medical device programmer, or an implantable medical device.

14. A system comprising:
processing circuitry configured to:
- receive an indication to enter a gesture control mode during which the processor is configured to control one or more actions related to a medical procedure;
- responsive to receiving the indication, enter the gesture control mode;
- monitor field input data received during the gesture control mode for one or more control gesture inputs, the one or more control gesture inputs requesting the processor control the one or more actions related to the medical procedure;
- determine, from the field input data, that an unexpected object is in an envelope within which the one or more control gesture inputs can be sensed, wherein the unexpected object is different than a user hand from which the one or more control gesture inputs are detectable; and
- responsive to determining that the unexpected object is in the envelope, suspending the gesture control mode to prevent detection of erroneous gesture input due to the unexpected object.

15. The system of claim 14, wherein the processing circuitry is configured to:
- determine to exit the gesture control mode; and
- responsive to determining to exit the gesture control mode, exit the gesture control mode, wherein exiting the gesture control mode disables gesture input control of the one or more actions related to the medical procedure.

16. The system of claim 15, wherein the processing circuitry is configured to determine to exit the gesture control mode by at least:
- monitoring a progress of the medical procedure, wherein the medical procedure comprises a plurality of steps, one step of the plurality of steps being configured to accept the one or more control gesture inputs controlling the one or more actions related to the medical procedure during the one step;
- determining that the one step of the medical procedure has been completed; and
- responsive to determining that the one step has been completed, exiting the gesture control mode.

17. The system of claim 16, wherein the one step is a first step of the plurality of steps, and wherein the one or more processors are configured to:
- accept the one or more control gesture inputs of a first plurality of gesture inputs during the first step;
- determine that the medical procedure has entered a second step of the plurality of steps of the medical procedure;
- responsive to the determination that the medical procedure has entered the second step of the plurality of steps of the medical procedure, enter the gesture control mode;
- accept one or more gesture inputs of a second plurality of gesture inputs during the second step, the second plurality of gesture inputs being different than the first plurality of gesture inputs;
- determine that the second step of the medical procedure has been completed; and
- responsive to determining that the second step has been completed, exit the gesture control mode for the second step.

18. The system of claim 14, wherein the processing circuitry is configured to determine to exit the gesture control mode by at least:

tracking a duration of time from when the gesture control mode was entered;
comparing the duration of time to a predetermined gesture control timeout;
determining that the duration of time exceeds the predetermined gesture control timeout; and
responsive to determining that the duration of time exceeds the predetermined gesture control timeout, exiting the gesture control mode.

19. The system of claim 14, wherein the field input data comprises first field input data received during the gesture control mode, and wherein the processing circuitry is configured to:
receive second field input data during the suspension of the gesture control mode;
detect, from the second field input data, that the unexpected object is no longer in the envelope; and
responsive to detecting that the unexpected object is no longer in the envelope, re-enter the gesture control mode.

20. The system of claim 14, wherein control of the one or more actions related to the medical procedure comprises adjustment of a parameter that at least partially defines a medical therapy.

21. The system of claim 14, wherein control the one or more actions of the medical procedure comprises control of a surgical device to operate with respect to a patient receiving the medical procedure.

* * * * *